US009364390B2

(12) United States Patent
Greiner et al.

(10) Patent No.: US 9,364,390 B2
(45) Date of Patent: Jun. 14, 2016

(54) IMPLANTABLE ELECTROACUPUNCTURE DEVICE AND METHOD FOR TREATING OBESITY

(71) Applicant: Valencia Technologies Corporation, Valencia, CA (US)

(72) Inventors: Jeffrey H. Greiner, Valencia, CA (US); David K. L. Peterson, Valencia, CA (US); Chuladatta Thenuwara, Castaic, CA (US); Stacy O. Greiner, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 234 days.

(21) Appl. No.: 13/736,039

(22) Filed: Jan. 7, 2013

(65) Prior Publication Data

US 2014/0214126 A1 Jul. 31, 2014

Related U.S. Application Data

(63) Continuation-in-part of application No. 13/622,497, filed on Sep. 19, 2012.

(60) Provisional application No. 61/606,995, filed on Mar. 6, 2012, provisional application No. 61/609,875, filed (Continued)

(51) Int. Cl.
*A61N 1/375* (2006.01)
*A61H 39/00* (2006.01)
(Continued)

(52) U.S. Cl.
CPC .......... *A61H 39/002* (2013.01); *A61N 1/36085* (2013.01); *A61N 1/36175* (2013.01);
(Continued)

(58) Field of Classification Search
CPC . A61N 1/32; A61N 1/36085; A61N 1/36089; A61N 1/3756; A61H 39/002

USPC .................. 607/2, 45, 59, 72, 116
See application file for complete search history.

(56) References Cited

U.S. PATENT DOCUMENTS

| 4,031,899 A | 6/1977 | Renirie |
| 4,157,720 A | 6/1979 | Greatbatch |

(Continued)

FOREIGN PATENT DOCUMENTS

| WO | WO 02/00294 A1 | 1/2002 |
| WO | WO 2014159433 A1 | 10/2014 |
| WO | WO 2014165111 A2 | 10/2014 |

OTHER PUBLICATIONS

Song, Kiseok, "The Compact Electro-Acupuncture System for Multi-Modal Feedback Electro-Acupuncture Treatment," 34th Annual International Conference of the IEEE EMBS, San Diego, CA, USA, Aug. 28,-Sep. 1, 2012.

(Continued)

*Primary Examiner* — William Levicky
(74) *Attorney, Agent, or Firm* — Bryant R. Gold

(57) ABSTRACT

An implantable electroacupuncture device (IEAD) treats obese conditions of a patient through application of stimulation pulses applied at acupoints SP4, LR8 or ST40, or their underlying nerves saphenous and peroneal. The IEAD comprises an implantable, coin-sized, self-contained, leadless electroacupuncture device having at least two electrodes attached to an outside surface of its housing. The device generates stimulation pulses in accordance with a specified stimulation regimen. Power management circuitry within the device allows a primary battery, having a high internal impedance, to be used to power the device. The stimulation regimen generates stimulation pulses during a stimulation session of duration T3 minutes applied every T4 minutes. The duty cycle, or ratio T3/T4, is very low, no greater than 0.05. The low duty cycle and careful power management allow the IEAD to perform its intended function for several years.

7 Claims, 20 Drawing Sheets

Related U.S. Application Data on Mar. 12, 2012, provisional application No. 61/672,257, filed on Jul. 16, 2012, provisional application No. 61/672,661, filed on Jul. 17, 2012, provisional application No. 61/673,254, filed on Jul. 19, 2012, provisional application No. 61/674,691, filed on Jul. 23, 2012, provisional application No. 61/676,275, filed on Jul. 26, 2012.

(51) Int. Cl.
| | |
|---|---|
| *A61N 1/372* | (2006.01) |
| *A61N 1/00* | (2006.01) |
| *A61N 1/36* | (2006.01) |
| *A61N 1/32* | (2006.01) |
| *A61N 1/378* | (2006.01) |

(52) U.S. Cl.
CPC .......... *A61N1/3756* (2013.01); *A61N 1/37205* (2013.01); *A61H 2201/5005* (2013.01); *A61H 2201/5038* (2013.01); *A61N 1/32* (2013.01); *A61N 1/36089* (2013.01); *A61N 1/36125* (2013.01); *A61N 1/36153* (2013.01); *A61N 1/36157* (2013.01); *A61N 1/3758* (2013.01); *A61N 1/3782* (2013.01); *Y10T 29/49208* (2015.01)

(56) References Cited

U.S. PATENT DOCUMENTS

| | | | |
|---|---|---|---|
| 4,345,604 | A | 8/1982 | Renirie |
| 4,528,072 | A | 7/1985 | Kurosawa |
| 4,535,784 | A | 8/1985 | Rohlicek |
| 4,566,064 | A | 1/1986 | Whitaker |
| 5,195,517 | A | 3/1993 | Chen |
| 5,199,428 | A | 4/1993 | Obel |
| 5,211,175 | A | 5/1993 | Gleason |
| 5,250,068 | A | 10/1993 | Ideguchi |
| 5,251,637 | A | 10/1993 | Kowloon |
| 5,372,605 | A | 12/1994 | Adams |
| 5,544,656 | A | 8/1996 | Pitsillides |
| 5,707,400 | A | 1/1998 | Terry |
| 5,891,181 | A | 4/1999 | Zhu |
| 6,006,134 | A | 12/1999 | Hill |
| 6,178,352 | B1 | 1/2001 | Gruzdowich |
| 6,393,324 | B2 | 5/2002 | Gruzdowich |
| 6,522,926 | B1 | 2/2003 | Kieval |
| 6,658,298 | B2 | 12/2003 | Gruzdowich |
| 6,735,475 | B1 | 5/2004 | Whitehurst |
| 6,839,596 | B2 | 1/2005 | Nelson |
| 6,950,707 | B2 | 9/2005 | Whitehurst |
| 6,978,174 | B2 | 12/2005 | Gelfand |
| 7,003,352 | B1 | 2/2006 | Whitehurst |
| 7,013,177 | B1 | 3/2006 | Whitehurst |
| 7,046,499 | B1 | 5/2006 | Imani |
| 7,136,701 | B2* | 11/2006 | Greatbatch et al. ............... 607/5 |
| 7,155,279 | B2 | 12/2006 | Whitehurst |
| 7,162,303 | B2 | 1/2007 | Levin |
| 7,171,266 | B2 | 1/2007 | Gruzdowich |
| 7,203,548 | B2 | 4/2007 | Whitehurst |
| 7,292,890 | B2 | 11/2007 | Whitehurst |
| 7,321,792 | B1 | 1/2008 | Min et al. |
| 7,373,204 | B2* | 5/2008 | Gelfand et al. ............... 607/44 |
| 7,440,806 | B1 | 10/2008 | Whitehurst |
| 7,444,180 | B2* | 10/2008 | Kuzma et al. ............... 607/2 |
| 7,610,100 | B2 | 10/2009 | Jaax |
| 7,620,451 | B2 | 11/2009 | Demarais |
| 7,657,316 | B2 | 2/2010 | Jaax |
| 7,962,219 | B2 | 6/2011 | Jaax |
| 8,805,512 | B1 | 8/2014 | Greiner |
| 2003/0078642 | A1 | 4/2003 | Malaney |
| 2003/0158588 | A1 | 8/2003 | Rizzo |
| 2003/0187485 | A1* | 10/2003 | Sturman et al. ............... 607/72 |
| 2003/0195583 | A1 | 10/2003 | Gruzdowich |
| 2003/0195585 | A1 | 10/2003 | Gruzdowich |
| 2005/0107832 | A1* | 5/2005 | Bernabei ............... 607/3 |
| 2005/0228460 | A1 | 10/2005 | Levin |
| 2005/0234533 | A1 | 10/2005 | Schulman |
| 2006/0041283 | A1 | 2/2006 | Gelfand |
| 2007/0005119 | A1 | 1/2007 | Crohn |
| 2007/0219595 | A1 | 9/2007 | He |
| 2007/0255319 | A1 | 11/2007 | Greenberg |
| 2007/0265680 | A1 | 11/2007 | Liu |
| 2008/0015572 | A1* | 1/2008 | Johnson et al. ............... 606/44 |
| 2008/0091255 | A1 | 4/2008 | Caparso |
| 2009/0192555 | A1 | 7/2009 | Schleicher |
| 2009/0210026 | A1 | 8/2009 | Solberg |
| 2009/0292341 | A1 | 11/2009 | Parramon |
| 2010/0069992 | A1 | 3/2010 | Aghassian |
| 2010/0211132 | A1 | 8/2010 | Nimmagadda |
| 2010/0324624 | A1 | 12/2010 | Chang |
| 2010/0327887 | A1 | 12/2010 | Denison |
| 2011/0106220 | A1 | 5/2011 | DeGiorgio |
| 2011/0112603 | A1 | 5/2011 | DeGiorgio |
| 2011/0172739 | A1 | 7/2011 | Mann |
| 2011/0218589 | A1 | 9/2011 | DeGiorgio |
| 2011/0218590 | A1 | 9/2011 | DeGiorgio |
| 2012/0022612 | A1 | 1/2012 | Littlewood |
| 2012/0259390 | A1 | 10/2012 | Canion |
| 2013/0041396 | A1 | 2/2013 | Ryotokuji |
| 2014/0214111 | A1 | 7/2014 | Greiner |
| 2014/0214112 | A1 | 7/2014 | Greiner |
| 2014/0214113 | A1 | 7/2014 | Greiner |
| 2014/0214114 | A1 | 7/2014 | Greiner |
| 2014/0214115 | A1 | 7/2014 | Greiner |
| 2014/0214116 | A1 | 7/2014 | Peterson |
| 2014/0214117 | A1 | 7/2014 | Greiner |
| 2014/0214118 | A1 | 7/2014 | Greiner |
| 2014/0214119 | A1 | 7/2014 | Greiner |
| 2014/0214124 | A1 | 7/2014 | Greiner |
| 2014/0214125 | A1 | 7/2014 | Greiner |
| 2014/0214126 | A1 | 7/2014 | Greiner |
| 2014/0214127 | A1 | 7/2014 | Greiner |
| 2014/0214128 | A1 | 7/2014 | Peterson |
| 2014/0214133 | A1 | 7/2014 | Thenuwara |
| 2014/0214134 | A1 | 7/2014 | Peterson |
| 2014/0214144 | A1 | 7/2014 | Peterson |

OTHER PUBLICATIONS

Cheung, et al., "The Mechanism of Acupuncture Therapy and Clinical Case Studies", (Taylor & Francis, publisher) (2001) ISBN-0-415-27254-8. Forward and Chapters 1-3, 5, 7, 8, 12 and 13.

Who Standard Acupuncture Point Locations in the Western Pacific Region. (World Health Organization Western Pacific Region, 2008, (updated and reprinted 2009), ISBN 978 92 9061 248 7. The Table of Contents, Forward (p. v-vi), General Guidelines for Acupuncture Point Locations (pp. 1-21), as well as pp. 64, 66, 71, 72, 74, 138 and 199.

"Acupuncture." http://en.wikipedia.org/wiki/Acupuncture.

'Electroacupuncture.' http://en.wikipedia.org/wiki/Electroacupuncture.

Lin, C. H., Lin, Y. M., & Liu, C. F. (2010). Electrical acupoint stimulation changes body composition and the meridian systems in postmenopausal women with obesity. The American Journal of Chinese Medicine, 38(04), 683-694.

Qunli W, Zhicheng L., Acupuncture treatment of simple obesity. J Tradit Chin Med 2005(2): 90-4.

"Acupuncture Today: Electroacupuncture". Feb. 1, 2004 (retrieved on-line Aug. 9, 2006 at http://www.acupuncturetoday.com/abc/electroacupuncture.php).

Cabioglu, M. T., Ergene, N. Electroacupuncture therapy for weight loss reduces serum total cholesterol, triglycerides, and LDL cholesterol levels in obese women. Am. J. Chin. Med. 33(4): 525-533, 2005.

Cabioglu, M.T., Ergene, N. Changes in serum leptin and beta endorphin levels with weight loss by electroacupuncture and diet restriction in obesity treatment. Am. J. Chin. Med. 34: 1-11, 2006.

Cabioglu MT, Ergene N, Tan U. Electroacupuncture Treatment of Obesity with Psychological Symptoms. Int. J. Neurosci 2007; 117: 579-90.

(56) References Cited

OTHER PUBLICATIONS

Cabioglu, M. T., Ergene, N., Surucu, H. S., Celik, H. & Findik, D. (2007). Serum IgG, IgA, IgM, and IgE levels after electroacupuncture and diet therapy in obese women. The American Journal of Chinese Medicine, 35(06), 955-965.

Cabioglue, M. T., & Ergene, N. (2006). Changes in level of serum insulin, C-peptide and glucose after electroacupuncture treatment and diet therapy in obese women. The American Journal of Chinese Medicine, 34(03), 367-376.

The Efficacy of Electroacupuncture Therapy for Weight Loss changes Plasma Lipoprotein A, Apoliprotein A and Apoliprotein B Levels in Obese Women. 2008. The American Journal of Chinese Medicine; 36 (06): 1029-1039.

Cheng Ling, Chen Miao-Gen, Yang Hui, et al., Influence of Acupuncture on Insulin Resistance in Simple Obesity Patients. J of Acupunct Tuina Sci; 2007, 5(4): 245-249.

Tian, DR, Li, XD, Shi, YS et all (2003) Study on the effect of transcutaneous electrical nerve stimulation on obesity. J. Peking Univ (Health Sci) 35: 277-279. English Translation.

Li-Qiu L, Wei-Zhi G, Xin D. Treatment of Simple Obesity of Stomach-Intestine Excessive Heat Type by Acupuncture and Tuina. J Acupunct Tuina Sci; 2005; 3(2): 61-62.

Li L, Wang ZY. Clinical therapeutic effects of body acupuncture and ear acupuncture on juvenile simple obesity and effects on metabolism of blood lipids. Zhongguo Zhen Jiu; 2006; 26(3): 173-6. English Translation.

Zhan M, Wang H. Observation on therapeutic effects of electroacupuncture for obesity polycystic ovary syndrome. J Acupunct Tuina Sci; 2008; 6(2) 90-93.

Hsu, C. H., Hwang, K. C., Chao, C. L., Lin, J. G., Kao, S. T., & Chou, P. (2005). Effects of electroacupuncture in reducing weight and waist circumference in obese women: a randomized crossover trial. International journal of obesity. 29(11), 1379-1384.

Rerksuppaphol, L., & Rerksuppaphol, S. (2011). Efficacy of electroacupuncture at the main acupoints for weight reduction in Thai obese women.

Tian, D., Li, X., Shi, Y., Liu, Y., & Han, J. (2003). Study on the effect of transcutaneous electric nerve stimulation on obesity. Beijing da xue xue bao. Yi xue ban=Journal of Peking University. Health Sciences, 35(3), 277. Chinese with English Translation.

Gucel, F, Bahar, B, Demirtas, C., Mit, S.. & Cevik C. (2012). Influence of acupuncture on leptin, ghrelin, insulin and cholecystokinin in obese women: a randomised, sham-controlled preliminary trial. Acupuncture in Medicine, 30(3), 203-207.

Peterson, U.S. Appl. No. 61/609,875, filed Mar. 12, 2012.
Greiner, U.S. Appl. No. 61/626,339, filed Sep. 23, 2011.
Peterson, U.S. Appl. No. 61/606,995, filed Mar. 6, 2012.
Thenuwara, U.S. Appl. No. 61/676,275, filed Jul. 26, 2012.
Greiner, U.S. Appl. No. 13/622,497, filed Sep. 19, 2012.
Peterson, U.S. Appl. No. 61/672,257, filed Jul. 16, 2012.
Peterson, U.S. Appl. No. 61/672,661, filed Jul. 17, 2012.
Peterson, U.S. Appl. No. 61/674,691, filed Jul. 23, 2012.
Peterson, U.S. Appl. No. 61/673,254, filed Jul. 19, 2012.

* cited by examiner

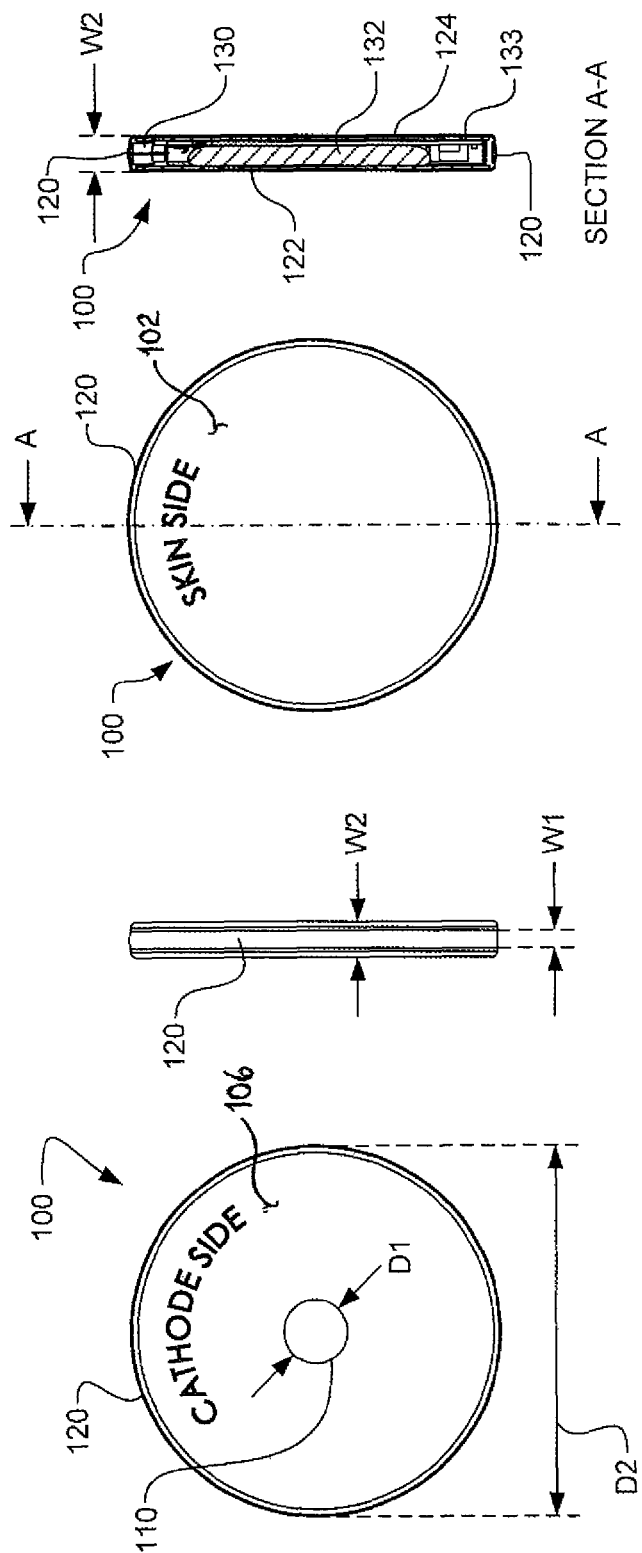

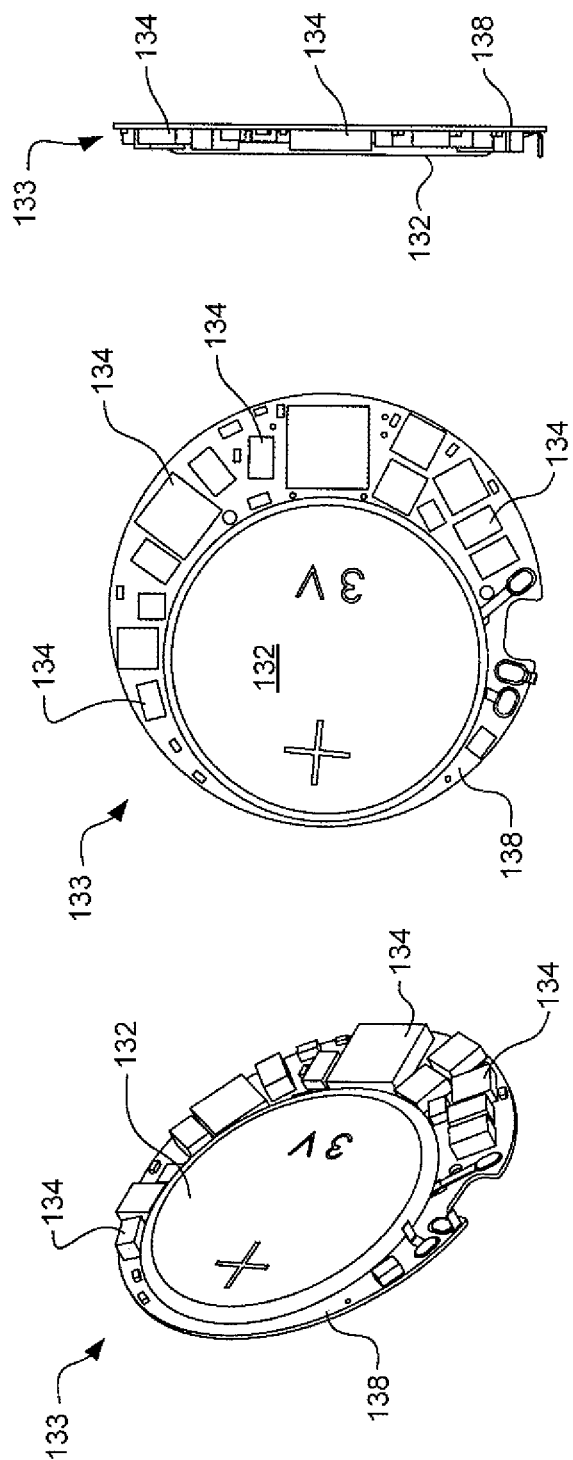

IMPLANTABLE ELECTROACUPUNCTURE DEVICE AND METHOD FOR TREATING OBESITY

RELATED APPLICATIONS

This application is a Continuation-In-Part (CIP) of U.S. patent application Ser. No. 13/622,497, filed Sep. 19, 2012, which application is incorporated herein by reference. This application also claims the benefit of the following previously-filed provisional patent applications, each of which is also incorporated herein by reference:

1. Electrode Configuration For Implantable Electroacupuncture Device, filed Mar. 6, 2012, Appl. No. 61/606,995, but see Publication No.: US 2014/0214144 A1, published Jul. 31, 2014;
2. Boost Converter Output Control For Implantable Electroacupuncture Device, filed Mar. 12, 2012, Appl. No. 61/609,875, but see Publication No.: US2014/0214128 A1, published Jul. 31, 2014;
3. Boost Converter Circuit Surge Control For Implantable Electroacupuncture Device Using Digital Pulsed Shutdown, filed Jul. 16, 2012, Appl. No. 61/672,257, but see Publication No.: US2014/0214128 A1, published Jul. 31, 2014;
4. Smooth Ramp-Up Stimulus Amplitude Control For Implantable Electroacupuncture Device, filed Jul. 17, 2012, Appl. No. 61/672,661, but see Publication No.: US2014/0214128 A1, published Jul. 31, 2014;
5. Battery Transient Current Reduction In An Implantable Electroacupuncture Device, filed Jul. 19, 2012, Appl. No. 61/673,254, but see Publication No.: US2014/0214128 A1, published Jul. 31, 2014;
6. Pulse Charge Delivery Control In An Implantable Electroacupuncture Device, filed Jul. 23, 2012, Appl. No. 61/674,691, but see Publication No.: US2014/0214128 A1, published Jul. 31, 2014;
7. Radial Feed-Through Packaging For An Implantable Electroacupuncture Device, filed Jul. 26, 2012, Appl. No. 61/676,275, but see Publication No.: US2014/0214133 A1 published Jul. 31, 2014.

BACKGROUND

Obesity is defined as having an excessive amount of body fat. Obesity is diagnosed by the Body Mass Index—a calculation of one's weight in relationship to height. A person with obesity has a body mass index (BMI) of 30 or higher. A person who is not considered obese but overweight has a body mass above 25 but below 30. Body mass index is calculated by dividing one's weight in kilograms by one's height in meters squared. However, muscular people and athletes may have a BMI in the obese category even though they may not have excess body fat; a person with great muscle mass with a BMI of 30 or higher may not be considered obese.

Although there are genetic and hormonal influences on body weight, obesity occurs when a person takes in more calories than he burns through exercise and normal daily activities. The body stores these excess calories as fat. Obesity usually results from a combination of causes and contributing factors, including:

1. Inactivity
2. Unhealthy diet and eating habits.
3. Pregnancy
4. Lack of sleep
5. Certain Medications.
6. Medical problems
7. Age
8. Social and economic issues According to the center for disease control and prevention, more than 1 third of U.S adults (35.7%) are obese. Obesity-related conditions include heart disease, stroke, type 2 diabetes, and certain types of cancer, which are some of the leading causes of preventable death. Obesity may also lead to high blood pressure, high cholesterol, metabolic syndrome, gallbladder disease, gynecologic problems, erectile dysfunction, skin problems, and osteoarthritis.

In 2008, medical costs associated with obesity were estimated at $147 billion; the medical costs for people who are obese were $1,429 higher than those of normal weight.

The most common treatments for obesity are dietary changes, exercise, surgery, and prescription weight loss medications. Unfortunately, these medications can have a high rate of inefficacy and often lead to unfortunate side effects. Side effects of these prescription drugs include oily and frequent bowel movements, bowel urgency, gas, headaches, dizziness, fatigue, nausea, dry mouth, insomnia, and constipation. Other rare but serious side effects include suicidal thoughts, psychiatric problems, and problems with memory or comprehension. Weight loss surgery is an option in some cases. It offers the best chance of high weight loss but contains serious risks. Gastric bypass surgery, laparoscopic adjustable gastric banding, gastric sleeve, and biliopancreatic diversion with duodenal switch are all surgical options. However, these procedures are all considered major invasive surgery. There are associated risks during surgery as well as risks for infection and malnutrition after surgery.

An alternative approach for treating obesity, diabetes, high cholesterol and a host of other physiological conditions, illnesses, deficiencies and disorders is acupuncture, which includes traditional acupuncture and acupressure. Acupuncture has been practiced in Eastern civilizations (principally in China, but also in other Asian countries) for at least 2500 years. It is still practiced today throughout many parts of the world, including the United States and Europe. A good summary of the history of acupuncture, and its potential applications may be found in Cheung, et al., "*The Mechanism of Acupuncture Therapy and Clinical Case Studies*", (Taylor & Francis, publisher) (2001) ISBN 0-415-27254-8, hereafter referred to as "Cheung, *Mechanism of Acupuncture*, 2001." The Forward, as well as Chapters 1-3, 5, 7, 8, 12 and 13 of Cheung, *Mechanism of Acupuncture*, 2001, are incorporated herein by reference.

Despite the practice in Eastern countries for over 2500 years, it was not until President Richard Nixon visited China (in 1972) that acupuncture began to be accepted in the West, such as the United States and Europe. One of the reporters who accompanied Nixon during his visit to China, James Reston, from the *New York Times*, received acupuncture in China for post-operative pain after undergoing an emergency appendectomy under standard anesthesia. Reston experienced pain relief from the acupuncture and wrote about it in The *New York Times*. In 1973 the American Internal Revenue Service allowed acupuncture to be deducted as a medical expense. Following Nixon's visit to China, and as immigrants began flowing from China to Western countries, the demand for acupuncture increased steadily. Today, acupuncture therapy is viewed by many as a viable alternative form of medical treatment, alongside Western therapies. Moreover, acupuncture treatment is now covered, at least in part, by most insurance carriers. Further, payment for acupuncture services consumes a not insignificant portion of healthcare expenditures in the U.S. and Europe. See, generally, Cheung, *Mechanism of Acupuncture*, 2001, vii.

Acupuncture is an alternative medicine that treats patients by insertion and manipulation of needles in the body at selected points. See, Novak, Patricia D. et al (1995). Dorland's Pocket Medical Dictionary (25th ed.), Philadelphia: (W.B. Saunders Publisher), ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map,". Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter(s) typically refers to a body organ, or other tissue location associated with, or affected by, that acupoint. However, usually only the letter(s), not the name of the body organ, is used in referring to the acupoint, but not always. Thus, for example, the acupoint SP4 is the same as acupoint Spleen 4 which is the same as SP-4 which is the same as SP 4 which is the same as Gongsun. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). The Table of Contents, Forward (page v-vi) and General Guidelines for Acupuncture Point Locations (pages 1-21), as well as pages 66, 71 and 199 (which illustrate with particularity the location of acupoints ST40, SP4 and LRB, respectively) are incorporated herein by reference. Moreover, the above-cited portions of the *WHO Standard Acupuncture Point Locations* 2008 reference book, with the exception of pages 66, 71 and 199, may be found as Appendix D in Applicant's earlier-filed patent application, U.S. patent application Ser. No. 13/622,497, filed Sep. 19, 2012, which application is incorporated herein by reference. The relevant information from pages 66, 71 and 199 of the *WHO Standard Acupuncture Point Locations* 2008 book is presented herein as FIG. 1A, 1B and 1C, and accompanying text, respectively.

While many in the scientific and medical community are highly critical of the historical roots upon which acupuncture has developed, (e.g., claiming that the existence of meridians, qi, yin and yang, and the like have no scientific basis), few can refute the vast amount of successful clinical and other data, accumulated over centuries of acupuncture practice, that shows needle manipulation applied at certain acupoints is quite effective.

The World Health Organization and the United States' National Institutes of Health (NIH) have stated that acupuncture can be effective in the treatment of neurological conditions and pain. Reports from the USA's National Center for Complementary and Alternative Medicine (NCCAM), the American Medical Association (AMA) and various USA government reports have studied and commented on the efficacy of acupuncture. There is general agreement that acupuncture is safe when administered by well-trained practitioners using sterile needles, but not on its efficacy as a medical procedure.

An early critic of acupuncture, Felix Mann, who was the author of the first comprehensive English language acupuncture textbook, *Acupuncture: The Ancient Chinese Art of Healing*, stated that "The traditional acupuncture points are no more real than the black spots a drunkard sees in front of his eyes." Mann compared the meridians to the meridians of longitude used in geography—an imaginary human construct. See, Mann, Felix (2000). *Reinventing acupuncture: a new concept of ancient medicine*. Oxford: Butterworth-Heinemann. pp. 14; 31. ISBN 0-7506-4857-0. Mann attempted to combine his medical knowledge with that of Chinese theory. In spite of his protestations about the theory, however, he apparently believed there must be something to it, because he was fascinated by it and trained many people in the West with the parts of it he borrowed. He also wrote many books on this subject. His legacy is that there is now a college in London and a system of needling that is known as "Medical Acupuncture". Today this college trains doctors and Western medical professionals only.

For purposes of this patent application, the arguments for and against acupuncture are interesting, but not that relevant. What is important is that a body of literature exists that identifies several acupoints within the human body that, rightly or wrongly, have been identified as having an influence on, or are otherwise somehow related to, the treatment of various physiological conditions, deficiencies or illnesses, including obesity or overweight conditions. With respect to these acupoints, the facts speak for themselves. Either these points do or do not affect the conditions, deficiencies or illnesses with which they have been linked. The problem lies in trying to ascertain what is fact from what is fiction. This problem is made more difficult when conducting research on this topic because the insertion of needles, and the manipulation of the needles once inserted, is more of an art than a science, and results from such research become highly subjective. What is needed is a much more regimented approach for doing acupuncture research.

It should also be noted that other medical research, not associated with acupuncture research, has over the years identified nerves and other locations throughout a patient's body where the application of electrical stimulation produces a beneficial effect for the patient. Indeed, the entire field of neurostimulation deals with identifying locations in the body where electrical stimulation can be applied in order to provide a therapeutic effect for a patient. For purposes of this patent application, such known locations within the body are treated essentially the same as acupoints—they provide a "target" location where electrical stimulation may be applied to achieve a beneficial result, whether that beneficial result is to reduce excess body fat, to treat cardiovascular disease, to treat mental illness, or to address some other issue associated with a disease or condition of the patient.

Returning to the discussion regarding acupuncture, some have proposed applying moderate electrical stimulation at selected acupuncture points through needles that have been inserted at those points. Such electrical stimulation is known as electroacupuncture (EA). According to *Acupuncture Today*, a trade journal for acupuncturists: "Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004 Feb. 1

U.S. Pat. No. 6,950,707, issued to Whitehurst et al., discloses use of an implantable miniature neurostimulator, referred to as a "microstimulator," that can be implanted into a desired tissue location and used as a therapy for treating obesity and eating disorders. The microstimulator has a tubular shape, with electrodes at each end.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,735,475 (headache and/or facial pain); U.S. Pat. No. 7,003,352 (epilepsy by brain stimulation); U.S. Pat. No. 7,013,177 (pain by brain stimulation); U.S. Pat. No. 7,155,279 (movement disorders through stimulation of Vagus nerve with both electrical stimulation and drugs); U.S. Pat. No. 7,292,890 (Vagus nerve stimulation); U.S. Pat. No. 7,203,548 (cavernous nerve stimulation); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain).

Techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize (i) large implantable stimulators having long leads that must be tunneled through tissue over an extended distance to reach the desired stimulation site, (ii) external devices that must interface with implanted electrodes via percutaneous leads or wires passing through the skin, or (iii) inefficient and power-consuming wireless transmission schemes. Such devices and methods are still far too invasive, or are ineffective, and thus subject to the same limitations and concerns, as are the previously described electrical stimulation devices.

From the above, it is seen that there is a need in the art for a less invasive device and technique for electroacupuncture stimulation of acupoints that does not require the continual use of needles inserted through the skin, or long insulated wires implanted or inserted into blood vessels, for the purposes of reducing excess body fat.

SUMMARY

One characterization of the invention described herein is an Implantable ElectroAcupuncture Device (IEAD) that treats obesity through application of electroacupuncture (EA) stimulation pulses applied at at least one of acupoints SP4, LR8 and ST40, or their underlying nerves, the peroneal and saphenous nerves. The IEAD includes: (1) a small IEAD housing having an electrode configuration thereon that includes at least two electrodes, (2) pulse generation circuitry located within the IEAD housing that delivers EA stimulation pulses to the patient's body tissue at one of the specified locations, (3) a primary battery also located within the IEAD housing that provides the operating power for the IEAD to perform its intended function, and (4) a sensor located within the IEAD housing that is responsive to operating commands wirelessly communicated to the IEAD from a non-implanted location, these operating commands allowing limited external control of the IEAD, such as ON/OFF and EA stimulation pulse amplitude adjustment.

In one preferred embodiment, the IEAD housing used as part of the invention is coin-sized and -shaped, having a nominal diameter of 23 mm, and a thickness of only 2 to 3 mm.

One preferred embodiment provides a symmetrical electrode configuration on the housing of the IEAD. Such symmetrical electrode configuration includes at least two electrodes, at least one of which is located substantially in the center of a first surface of the IEAD housing, and is referred to as a central electrode. The other electrode is symmetrically positioned around and at least 5 mm distant from the center of the central electrode, and is referred to as an annular or ring electrode (or, in some instances, as a circumscribing electrode). This symmetry between the central electrode and the annular electrode advantageously focuses the electric field, and hence the EA stimulation current created by application of an EA stimulation pulse to the electrodes, deep into the tissue below the central electrode, where the desired EA stimulation occurs. Hence, when implanted, the first surface of the IEAD housing is faced inwardly into the patient's tissue below a specified location on the surface of the patient's skin, e.g., a specified acupoint, and a second surface of the IEAD housing, on the opposite side of the housing from the first surface, is faced outwardly to the patient's skin. One preferred embodiment of the IEAD housing uses one centrally located cathode electrode on the first surface of the IEAD housing, and one ring anode electrode located on a perimeter edge of a coin-sized and -shaped IEAD housing.

The pulse generation circuitry located within the IEAD housing is coupled to the at least two electrodes. This pulse generation circuitry is configured to generate EA stimulation pulses in accordance with a specified stimulation regimen. This stimulation regimen defines the duration and rate at which a stimulation session is applied to the patient. The stimulation regimen requires that the stimulation session have a duration of no more than T3 minutes and a rate of occurrence of no more than once every T4 minutes. Advantageously, the duty cycle of the stimulation sessions, i.e., the ratio of T3/T4, is very low, no greater than 0.05. A representative value for T3 is 30 minutes, and a representative value for T4 is 7 days. The individual EA stimulation pulses that occur within the stimulation session also have a duty cycle measured relative to the period (the inverse of the frequency or rate of the stimulation pulses) of no greater than 1%. A representative pulse width and frequency for the EA stimulation pulses is 0.1 milliseconds, occurring at a pulse rate of 2 Hz.

The primary battery contained within the IEAD housing and electrically coupled to the pulse generation circuitry has a nominal output voltage of 3 volts, and an internal battery impedance that is at least 5 ohms, and may be as high as 150 ohms or more. Advantageously, electronic circuitry within the IEAD housing controls the value of the instantaneous surge current that may be drawn from the battery in order to prevent any large drops in the battery output voltage. Avoiding large drops in the battery output voltage assures that the circuits within the IEAD will continue to operate as designed without failure. Being able to use a primary battery that has a relatively high internal impedance allows the battery to be thinner, and thus allows the device to be thinner and more easily implanted. The higher internal impedance also opens the door to using relatively inexpensive commercially-available disc batteries as the primary battery within the IEAD, thereby greatly enhancing the manufacturability of the IEAD and significantly lowering its cost.

Another characterization of the invention described herein may be described as a first method for treating patients with obesity or excess body fat using a leadless, coin-sized implantable electroacupuncture device (IEAD). Such IEAD is powered by a small disc battery having a specified nominal output voltage of about 3.0 volts, and having an internal impedance of at least 5 ohms.

The IEAD used to practice this first method is configured, using electronic circuitry within the IEAD, to generate EA stimulation pulses in accordance with a specified stimulation regimen. The EA stimulation pulses generated in accordance with this stimulation regimen are applied to the patient's tissue through at least two electrodes located on the housing of the IEAD. These two electrodes include at least one central electrode, located in the center of a bottom surface of the IEAD housing, and at least one annular electrode that surrounds the central electrode. The edge of the annular electrode closest to the central electrode is separated from the center of the central electrode by at least 5 mm.

Using such an IEAD, the obesity treatment provided by this first method includes the steps of: (a) implanting the IEAD below the skin surface of the patient at acupoint SP4, LR8 or ST40, or at a target location on the skin surface above the peroneal or saphenous nerves, with a bottom surface of the IEAD (the "bottom" surface of the IEAD is that surface on which the central electrode is placed) facing into the patient's tissue below the patient's skin surface at the target location; and (b) enabling the IEAD to provide stimulation pulses in accordance with a specified stimulation regimen.

The specified stimulation regimen, when enabled, provides a stimulation session at a rate of once every T4 minutes, with each stimulation session having a duration of T3 minutes. The ratio of T3/T4 is no greater than 0.05. A preferred stimulation session time T3 is 30 minutes, but T3 could be as short as 10 minutes or as long as 60 minutes. A preferred time between stimulation sessions T4 is 7 days, but it could be as short as 1 day or as long as 14 days, as needed, to suit the needs of a particular patient.

Yet another characterization of the invention described herein is a second method for treating patients with obesity. This second method includes: (a) implanting a coin-sized electroacupuncture (EA) device in the patient just below the patient's skin at a target stimulation site that includes at least one of acupoints SP4, LR8 and ST40, or their underlying nerves, the peroneal and saphenous nerves; (b) enabling the EA device to generate EA stimulation sessions at a duty cycle that is less than 0.05, wherein each stimulation session comprises a series of EA stimulation pulses; and (c) delivering the EA stimulation pulses of each stimulation session to the target stimulation site through at least two electrodes attached to an outside surface of the EA device. The duty cycle of the stimulation sessions is the ratio of T3/T4, where T3 is the duration in minutes of each stimulation session, and T4 is the time in minutes between stimulation sessions.

In a preferred application for this second method, the electrodes attached to the outside surface of the EA device are arranged in a symmetrical pattern. This symmetrical pattern of electrodes advantageously concentrates, or focuses, the electric field emanating from the electrode(s) downward into the tissue below the target stimulation site to a location where the electroacupuncture stimulation is most effective.

Additionally, the invention described herein may be characterized as a method of assembling an implantable electroacupuncture device (IEAD) for use in treating obesity. The IEAD is assembled so as to reside in a round, thin, hermetically-sealed, coin-sized housing. An important feature of the coin-size housing, and the method of assembly associated therewith, is that it electrically and thermally isolates a feed-through pin assembly radially passing through a wall of the coin-sized housing from the high temperatures associated with welding the housing closed to hermetically seal its contents. Such method of assembling includes the steps of:

a. forming a coin-sized housing having a bottom case and a top cover plate, the top cover plate being adapted to fit over the bottom case, the bottom case being substantially round and having a diameter D2 that is nominally 23 mm and a perimeter side wall extending all the way around the perimeter of the bottom case, the perimeter side wall having a height W2, wherein the ratio of W2 to D2 is no greater than about 0.13;

b. forming a recess in one segment of the side wall, the recess extending radially inwardly from the side wall to a depth D3, and the recess having an opening in a bottom wall portion thereof;

c. hermetically sealing a feed-through assembly in the opening in the bottom of the recess, the feed-through assembly having a feed-through pin that passes through the opening without contacting the edges of the opening, a distal end of the pin extending radially outward beyond the side wall of the bottom case, and a proximal end of the feed-through pin extending radially inward toward the center of the bottom case, whereby the feed-through pin assembly is hermetically bonded to the opening in the side wall at a location in the bottom of the recess that is a distance D3 from the perimeter side wall, thereby thermally isolating the feed-through assembly from the high temperatures that occur at the perimeter side wall when the cover plate is welded to the edge of the perimeter side wall;

d. attaching a central electrode to the thin, coin-sized housing at a central location on the bottom outside surface of the feed-through housing;

e. inserting an electronic circuit assembly, including a battery, inside of the bottom case, and connecting the proximal end of the feed-though pin to an output terminal of the electronic circuit assembly, and electrically connecting the bottom case to a reference terminal of the battery;

f. baking out the assembly to remove moisture, back filling with a mixture of He/Ar inert gas, and then welding the top cover plate to the edges of the side wall of the bottom case, thereby hermetically sealing the electronic circuit assembly, including the battery, inside of the thin, coin-sized IEAD housing;

g. leak testing the welded assembly to assure a desired level of hermeticity has been achieved;

h. placing an insulating layer of non-conductive material around the perimeter edge of the thin coin-sized housing, then placing a circumscribing electrode over the insulating layer of non-conductive material, and then electrically connecting the distal end of the feed-through pin to the circumscribing electrode; and i. covering all external surface areas of the thin, coin-sized housing with a layer of non-conductive material except for the circumscribing electrode around the perimeter of the coin-sized housing and the central electrode centrally located on the bottom surface of the thin-coin-sized housing.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 2 shows a plan view of one surface of the IEAD housing illustrated in FIG. 1.

FIG. 2A shows a side view of the IEAD housing illustrated in FIG. 1.

FIG. 3 shows a plan view of the other side, indicated as the "Back Side," of the IEAD housing or case illustrated in FIG. 1.

FIG. 3A is a sectional view of the IEAD of FIG. 3 taken along the line A-A of FIG. 3.

FIG. 6 is a perspective view of an electronic assembly, including a battery, that is adapted to fit inside of the empty housing of FIG. 4 and FIG. 5.

FIGS. 6A and 6B show a plan view and side view, respectively, of the electronic assembly shown in FIG. 6.

Figure 1:
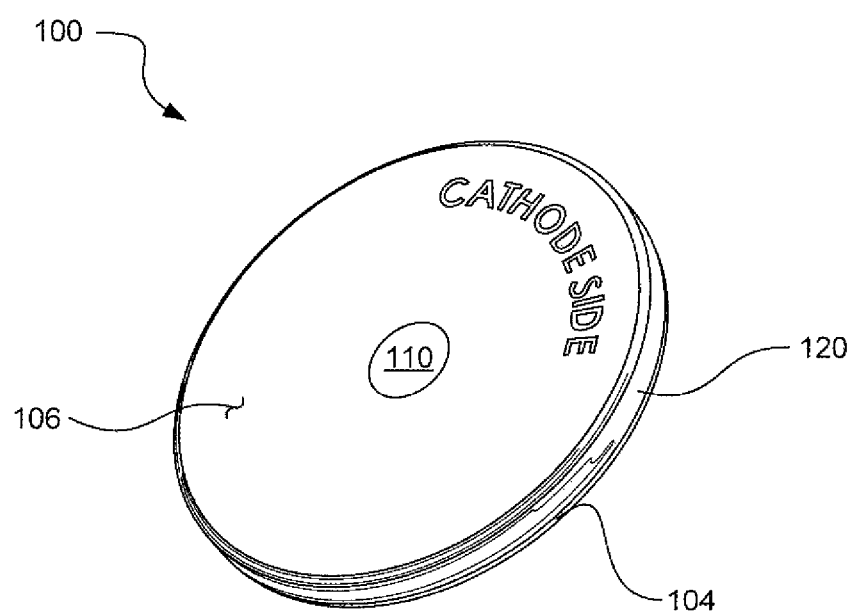
FIG. 1 is a perspective view of an Implantable Electroacupuncture Device (IEAD) made in accordance with the teachings presented herein.

Appendix A illustrates some examples of alternate symmetrical electrode configurations that may be used with an IEAD of the type described herein. Appendix A is not submitted herewith, but is found as Appendix A submitted with Applicant's earlier patent application, U.S. patent application Ser. No. 13/622,497, filed Sep. 19, 2012, (the "Parent" application of this application), which Parent application has been previously incorporated herein by reference.

Appendix B illustrates a few examples of non-symmetrical electrode configurations that may be used with an IEAD made in accordance with the teachings herein. Appendix B is not submitted herewith, but is incorporated herein by reference, and may be found as Appendix B submitted with Applicant's earlier-filed Parent application (Ser. No. 13/622,497, filed Sep. 19, 2012).

Appendix C shows an example of the code used in the micro-controller IC (e.g., U2 in FIG. 14) to control the basic operation and programming of the IEAD, e.g., to turn the IEAD ON/OFF, adjust the amplitude of the stimulus pulse, and the like, using only an external magnet as an external communication element. Appendix C is not submitted herewith, but is incorporated herein by reference, and may be found as Appendix C submitted with Applicant's earlier-filed Parent application (Ser. No. 13/622,497, filed Sep. 19, 2012).

Appendices A, B, and C of Applicant's earlier-filed Parent application are incorporated by reference herein.

Throughout the drawings and appendices, identical reference numbers designate similar, but not necessarily identical, elements.

DETAILED DESCRIPTION

Overview

Disclosed and claimed herein is an implantable, coin-shaped, self-contained, leadless electroacupuncture (EA) device having at least two electrode contacts mounted on the surface of its housing. As disclosed herein, the EA device is adapted to treat obesity of a patient. In one preferred embodiment, the electrodes on the surface of the EA device housing include a central cathode electrode on a bottom side of the housing, and an annular anode electrode that surrounds the cathode. In another preferred embodiment, the anode annular electrode is a ring electrode placed around the perimeter edge of the coin-shaped housing.

The EA device is leadless. This means there are no leads or electrodes at the distal end of leads (common with most implantable electrical stimulators) that have to be positioned and anchored at a desired stimulation site. Also, because there are no leads, no tunneling through body tissue or blood vessels is required in order to provide a path for the leads to return and be connected to a tissue stimulator (also common with most electrical stimulators).

The EA device is adapted to be implanted through a very small incision, e.g., less than 2-3 cm in length, directly adjacent to a selected target stimulation site, e.g., an acupuncture site ("acupoint") known to moderate or affect an obese condition of a patient.

The EA device is easy to implant. Also, most embodiments are symmetrical. This means that there is no way that it can be implanted incorrectly (unless the physician puts it in up-side-down, which would be difficult to do given the markings on its case). All that need be done is to cut the incision, and slide the device in place through the incision. Once the implant pocket has been prepared, it is as easy as sliding a coin into a slot. Such implantation can usually be completed in less than 10 minutes in an outpatient setting, or in a doctor's office. Only minor, local anesthesia need be used. No major or significant complications are envisioned for the implant procedure. The EA device can also be easily and quickly explanted, if needed.

The EA device is self-contained. It includes a primary battery to provide its operating power. It includes all of the circuitry it needs, in addition to the battery, to allow it to perform its intended function for several years. Once implanted, the patient will not even know it is there, except for a slight tingling that may be felt when the device is delivering stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can do so using, e.g., an external magnet.

The EA device can operate for several years because it is designed to be very efficient. Stimulation pulses applied by the EA device at a selected target stimulation site, e.g., a specified acupoint, through its electrodes formed on its case are applied at a very low duty cycle in accordance with a specified stimulation regimen. The stimulation regimen applies EA stimulation during a stimulation session that lasts at least 10 minutes, typically 30 minutes, and rarely longer than 60 minutes. These stimulation sessions, however, occur at a very low duty cycle. In one preferred treatment regimen, for example, a stimulation session having a duration of 30 minutes is applied to the patient just once a week. The stimulation regimen, and the selected acupoint at which the stimulation is applied, are designed and selected to provide efficient and effective EA stimulation for the treatment of the patient's obese condition.

The EA device is, compared to most implantable medical devices, relatively easy to manufacture and uses few components. This not only enhances the reliability of the device, but helps keep the manufacturing costs low, which in turn allows the device to be more affordable to the patient. One key feature included in the mechanical design of the EA device is the use of a radial feed-through assembly to connect the electrical circuitry inside of its housing to one of the electrodes on the outside of the housing. The design of this radial feed-through pin assembly greatly simplifies the manufacturing process. The process places the temperature sensitive hermetic bonds used in the assembly—the bond between a pin and an insulator and the bond between the insulator and the case wall—away from the perimeter of the housing as the housing is hermetically sealed at the perimeter with a high temperature laser welding process, thus preserving the integrity of the hermetic bonds that are part of the feed-through assembly.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

Another key feature included in the design of the EA device is the use of a commercially-available battery as its primary power source. Small, thin, disc-shaped batteries, also known as "coin cells," are quite common and readily available for use with most modern electronic devices. Such batteries come in many sizes, and use various configurations and materials. However, insofar as inventors or applicant are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible, and so that dips in the battery output voltage (caused by any sudden surge in instantaneous battery current) do not occur that could compromise the performance of the device. Furthermore, the energy requirements of other active implantable therapies are far greater than can be provided by such coin cells without frequent replacement.

The EA device disclosed herein advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Moreover, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture and to provide it to patients at an affordable cost.

A preferred application for an EA device made in accordance with the teachings presented herein is to treat the condition of having excess body fat, whether a patient is considered obese. Thus, the description that follows describes in much more detail an EA device that is especially suited to be used to treat excess body fat. However, it is to be understood that the invention is not limited to treating only excess body fat.

DEFINITIONS

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−(0.05×23 mm=1.15 mm). "Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

As explained in more detail below, the essence of the invention recognizes that an electroacupuncture modulation scheme need not be continuous, thereby allowing the implanted EA device to use a small, high density, power source to provide such non-continuous EA modulation. (Here, it should be noted that "EA modulation," as that phrase is used herein, is the application of electrical stimulation pulses, at low intensities, low frequencies and low duty cycles, to at least one of the target stimulation sites, e.g., acupuncture sites, that has been identified as affecting a particular condition, e.g., excess body fat. As a result, the EA device can be very small. And, because the electrodes form an integral part of the housing of the EA device, the EA device may thus be implanted directly at (or very near to) the desired target tissue location, e.g., the target stimulation site, such as the target acupoint.

In summary, and as explained more fully below in conjunction with the description of the treatment method for removing excess body fat, the basic approach of EA stimulation includes: (1) identify an acupoint(s) or other target stimulation site that may be used to treat or mediate the particular illness, condition or deficiency that has manifest itself in the patient; (2) implant an EA device, made as described herein, so that its electrodes are firmly anchored and located so as to be near or on the identified acupoint(s) or other target stimulation site; (3) apply EA modulation, having a low intensity, low frequency, and low duty cycle through the electrode(s) of the EA device so that electrical stimulation pulses flow through the tissue at the target acupoint(s) following a prescribed stimulation regimen over several weeks or months or years. At any time during this EA stimulation regimen, the patient's illness, condition or deficiency may be evaluated and, as necessary, the parameters of the EA modulation applied during the EA stimulation regimen may be adjusted or "tweaked" in order to improve the results obtained from the EA modulation.

Conditions Treated

Overweight and obesity are both terms used for characterizing patients exhibiting an excess of body fat. Obesity is generally diagnosed by a patient's body mass index (BMI), which is a calculation of weight in relationship to height. Generally it is a good measure of whether a patient has excess body fat. However, in cases where a patient has more muscle than average, the patient may not be obese despite a calculation which would suggest obesity. While BMI correlates with body fat, it does not directly measure body fat. A BMI of 30 or above is generally indicative of obesity. Similarly, a BMI between 25 and 29.9 is generally indicative of an overweight state and an excess of body fat. There exist other methods of estimating body fat such as skinfold thickness and waist circumference, a calculation of waist to hip ratio, and other techniques such as ultrasound, computed tomography, and magnetic resonance imagine (MRI).

The carrying of excess body fat has serious consequences to one's health. In particular, obesity and being overweight are strong risk factors for a number of conditions such as cardiovascular diseases (particularly heart disease and stroke), diabetes, musculosketal disorders, especially osteoarthritis, and endometrial, colon and breast cancers.

Obesity has become a greater problem in recent years, having more than doubled in prevalence worldwide since 1980. Obesity and overweight are the fifth leading risk for global deaths. It is a serious problem worldwide, and even more so in industrialized nations like the United States.

Applicant has identified a handful of studies utilizing electroacupuncture or manual acupuncture for the treatment of obese and overweight patients with some success. While most of the studies are conducted over an inadequate time period for the achievement of a healthy weight, e.g. twenty days, the quality and results of a handful of studies are compelling Among the most compelling studies are several conducted by Cabioglu et al in Turkey. Cabioglu et al conducted six studies for which the same electrical stimulation parameters were utilized and over a period of twenty days for the treatment of obesity. See, Cabioglu, M. T. and N. Ergene. Electroacupuncture therapy for weight loss reduces serum total cholesterol, triglycerides, and LDL cholesterol levels in obese women. Am. J. Chin. Med. 33(4): 525-533, 2005 (hereafter, "Cabioglu 2005"); Cabioglu, M. T. and N. Ergene.

Changes in serum leptin and beta endorphin levels with weight loss by electroacupuncture and diet restriction in obesity treatment. Am. J. Chin. Med. 34: 1-11, 2006 (hereafter, "Cabioglu 2006"); Cabioğlu MT, Ergene N, Tan U. Electroacupuncture Treatment of Obesity with Psychological Symptoms. Int. J. Neurosci 2007, 117: 579-90 (hereafter, Cabioglu 2007"); Cabioglu, M. T., Ergene, N., Surucu, H. S., celik, H. H., & Findik, D. (2007). Serum IgG, IgA, IgM, and IgE levels after electroacupuncture and diet therapy in obese women. *The American journal of Chinese medicine,* 35(06), 955-965 (hereafter, "Cabioglu et al 2007"); Cabioglu, M. T., & Ergene, N. (2006). Changes in levels of serum insulin, C-peptide and glucose after electroacupuncture and diet therapy in obese women. *The American journal of Chinese medicine,* 34(03), 367-376 (hereafter, "Cabioglu, Ergene 2006); The Efficacy of Electroacupuncture Therapy for Weight Loss changes Plasma Lipoprotein A, Apoliprotein A and Apoliprotein B Levels in Obese Women. 2008. The American Journal of Chinese Medicine; 36 (06):1029-1039 (hereafter, "Cabioglu 2008").

In addition to the measurement of weight loss and weight loss as a percentage of baseline weight, the group measured chemicals known to be associated with obesity and changes in weight. Patients lost an average of four and a half to five percent body weight over twenty days of electroacupuncture therapy conducted by the group in six different studies. Like most acupuncture, several points were stimulated or manipulated. The group includes auricular (or ear) acupuncture as well as four to five body acupoints in their regimen, which were stimulated bilaterally (one on each side of the body). However, unlike how traditional Chinese medicine is generally conducted, the treatment was not personalized; patients in each study received the same number and same acupoints. Such a treatment regimen allows for repeatability and better evaluation of the use of the particular points.

More importantly, when four points were utilized by Cabioglu et al, only three nerves directly underlie those points, better narrowing the necessary trigger points. While Applicant believes the acupoints and not the nerves alone are responsible for the bringing about of some good through electrical stimulation, it has used cross-sectional anatomy of certain points associated with success and the identification of common nerves to narrow the sphere of acupoints. For repeatability and the practicality of placing an implantable device at only a couple of acupoints, Applicant narrowed its focus to several acupoints. The two nerves underlying most points deduced to be largely responsible for weight loss in acupuncture studies are the saphenous nerve and the peroneal nerve.

Applicant vigorously searched for efficacious obesity studies utilizing the science of acupuncture. The search led to the discovery of a handful of studies with good efficacy and the deduction that several points may be more efficacious than others. In particular, applicant has identified three points believed to be responsible for many of the positive results in obesity studies and most accessible for implantation of the device. Those points are SP4 ("Gongsun"), LR8 ("Ququan"), and ST40 ("Fenglong"). While Applicant has not uncovered a single study utilizing only those points together or one of those points alone for the achievement of weight loss, Applicant has determined that the aforementioned points are a combination most responsible for the positive results and most accessible.

In a study called, "Study on the Effect of Transcutaneous Electric Nerve Stimulation on Obesity," sixteen patients underwent transcutaneous electric nerve stimulation ("TENS") on five acupoints and achieved weight loss. See, Tian D R, Li X D, Shi Y S et al (2003) Study on the effect of transcutaneous electric nerve stimulation on obesity. J Peking Univ (Health Sci) 35:277-279. English Translation (hereafter, "Tian 2003"). Those five acupoints included one of the chosen points, SP4. Patients lost about 3.9% of their baseline weight (which baseline weight averaged 72 kilograms). From an analysis of many obesity studies, applicant believes that those acupoints overlying the saphenous and the peroneal nerve are most active in bringing about weight loss. In the Tian study, the only acupoint overlying one of those nerves, the saphenous nerve, is SP4. Because SP4 is also more ideally situated on the body than some acupoints overlying seeply situated nerve targets, Applicant has narrowed its focus to SP4 alongside the other two points for this application.

In another study for which manual acupuncture was utilized in obese patients with success, four points were manually stimulated with an acupuncture needle. See, Qunli W, Zhicheng L. Acupuncture treatment of simple obesity. J Tradit Chin Med 2005(2):90-4 (hereafter, "Qunli 2005"). The acupoints were BL18, LR8, GB43, and LR3. Applicant believes acupoints LR8 and LR3 are most responsible for the weight loss achieved in this study. Given that LR8 is better situated for an implantation of coin-sized device, Applicant has excluded LR3 from this patent. In this study, 5.2% weight loss was achieved in five people over twenty four days or twelve treatment days.

Furthermore, in six of the studies Applicant considers efficacious in the use of acupuncture for the treatment of obesity, one acupoint, ST40, is utilized in addition to several other points. See, e.g. Tian 2003, Qunli 2005, Li L, Wang Z Y. Clinical therapeutic effects of body acupuncture and ear acupuncture on juvenile simple obesity and effects on metabolism of blood lipids. Zhongguo Zhen Jiu; 2006; 26(3):173-6. English Translation (hereafter, "Li 2006"); Zhan M, Wang H. Observation on therapeutic effects of electroacupuncture for obesity polycystic ovary syndrome. J Acupunct Tuina Sci; 2008; 6(2):90-93 (hereafter, "Zhan 2008"); Li-qiu L, Wei-zhi G, Xin D. Treatment of Simple Obesity of Stomach-Intestine Excessive Heat Type by Acupuncture and Tuina. J Acupunct Tuina Sci; 2005; 3(2):61-62 (hereafter, Li-qiu 2005"); Cheng Ling, Chen Miao-gen, YANG Hui, et al. Influence of Acupuncture on Insulin Resistance in Simple Obesity Patients. J of Acupunct Tuina Sci; 2007, 5(4): 245-249 (hereafter, "Cheng 2007").

In particular, the efficacy was notable in a study conducted by Cheng et al. for which ten acupoints were manually stimulated in fifty obese patients (Cheng 2007). Low-frequency electroacupuncture was also utilized at acupoint ST40 alongside a few other acupoints. (Note that acupoint ST40 is one of the three acupoints identified herein for treating obesity.) Over about 15 treatment days, patients lost about 4.5% of their baseline weight.

Regarding the process of selection of acupoints SP4, LRB, and ST40, Applicant identifies several studies for which multiple acupoints were stimulated either with electroacupuncture, transcutaneous electric stimulation, or manually, and successful weight loss was achieved. Given vigorous studies conducted by a group in Turkey using only four or five acupoints, Applicant was able to make a deduction about which acupoints are likely to be most responsible for the positive results when compared to studies utilizing more acupoints and achieving success with most similar stimulation parameters. See, Cabioglu 2005; Cabioglu et al. 2007; Cabioglu 2007; Cabioglu, Ergene 2006; Cabioglu 2006; Cabioglu 2008. In particular, Applicant excludes two of four points always utilized in the Cabioglu et al studies at hand because they are not commonly included (or their primary underlying nerve) in other acupuncture studies bringing about weight loss in overweight patients. See, e.g. Cheng 2007. Those points are LI4 and LI11. Rather, Applicant believes ST36 and ST44 which overlie the saphenous and peroneal nerves are primarily responsible for Cabioglu's patients' weight loss. Since other acupoints also involved in successful studies and overlying the identified nerves are more suitable sites for implantation, Applicant excludes ST36 and ST44 from this particular patent.

While the mechanism underlying the successful results from electroacupuncture, TENS, and manual acupuncture is not clearly drawn out, there are some hints showing the involvement of certain hormones. In particular, in a study conducted by Cabioglu and another by Gucel for which the chemical leptin was measured, the achievement of weight loss from electroacupuncture or manual acupuncture was also accompanied by reductions in leptin. See, e.g. Cabioglu 2006, Gucel 2012. Leptin is thought to be involved in appetite. Leptin is one of the products of adipose tissue, which passes through the blood-brain barrier and reduces appetite.

Furthermore, in Gucel's study between-group analyses demonstrated increases in plasma ghrelin and Cholecystokinin (CCK) levels in subjects who received acupuncture treatment. See, Gucel 2012. CCK is a neurotransmitter causing satiety after a meal by affecting the central nervous system, and hence it has close relationship with ghrelin. CCK secretion has been shown to decrease hunger. An increase of ghrelin, on the other hand, is known to increase appetite and bring about weight gain. Thus, the increase in ghrelin in Gucel's study is not reconciled with the results of weight loss.

Additionally, beta endorphin (BE) levels may be involved in the mechanism. Cabioglu's group said that in their patients, rising serum BE level probably enhanced the lipolitic activity which may have caused weight loss in obese people by mobilizing energy stores. See, Cabioglu 2006.

Thus, it appears evident that a few hormones exist that are involved in the reduction of weight loss from acupuncture, whether achieved through electroacupuncture, TENS at acupoints, or manual acupuncture.

Locations Stimulated and Stimulation Paradigms/Regimens

Applicant has identified three acupoints most responsible and most ideal for application of its technological approach to treat obesity. Those acupoints are SP4, LR8, and ST40. The nerves underlying these three acupoints—the saphenous and peroneal nerves—have also been identified as target stimulation points to treat obesity.

The acupoint SP4, also called "Gongsun," is located on the medial side of the foot when in a seated position, in the fossa distal and inferior to the base of the first metatarsal. See, *WHO Standard Acupuncture Point Locations* 2008, page 71. See also FIG. 1A. SP4 is located in the depression distal to the base of the first metatarsal bone. It may be identified as SP4 or SP 4 or Spleen 4 or Gongsun; each name refers to the same point. Additionally, it is possible, given the breadth of acupuncture practice across the world, there exists another name or spelling for SP4 less commonly used. For the purpose of simplicity, Applicant refers to the point as either SP4 or Gongsun.

The acupoint LR8, also called "Ququan," is located on the medial aspect of the knee, in the depression medial to the tendons of the semitendinosus and the semimenbranosus muscles, at the medial end of the popliteal crease. See, *WHO Standard Acupuncture Point Locations* 2008, page 199. See also FIG. 1B. With the knee flexed, LR8 is located in the depression medial to the most prominent tendon on the medial end of the popliteal crease. The acupoint may be identified as LR8, Liv 8, LR 8, Liver 8, or Ququan; each name refers to the same point. However, it is possible there are other names identifying the same point. Herein, Applicant identifies the point as LR8 or Ququan.

The acupoint ST40, also called "Fenglong," is located on the anterolateral aspect of the leg, at the lateral border of the tibialis anterior muscle, about 8 B-cun superior to the prominence of the lateral malleolus. See, *WHO Standard Acupuncture Point Locations* 2008, page 66. See also FIG. 1C. (Note: "8 B-cun" is a proportional bone (skeletal) measurement, and is explained in *WHO Standard Acupuncture Point Locations* 2008, pages 11-13, previously included in the material incorporated herein by reference.) The location of acupoint ST40 is also identified as about one fingerbreadth (a middle finger) lateral to its neighboring point, ST38. It is called ST40, ST 40, Stomach 40, Fenglong, among other names; each name refers to the same acupoint. Herein, Applicant identifies this acupoint as ST40 or Fenglong.

High-frequency stimulation is less successful at bringing about weight loss in overweight patients when compared to low-frequency stimulation paradigms that are otherwise similar in acupoint selection or stimulation paradigm. See, e.g. Lin, C. H., Lin, Y. M., & Liu, C. F. (2010). Electrical acupoint stimulation changes body composition and the meridian systems in postmenopausal women with obesity. *The American Journal of Chinese Medicine,* 38(04), 683-694 (hereafter, "Lin 2010"); Hsu, C. H., Hwang, K. C., Chao, C. L., Lin, J. G., Kao, S. T., & Chou, P. (2005). Effects of electroacupuncture in reducing weight and waist circumference in obese women: a randomized crossover trial. *International journal of obesity,* 29(11), 1379-1384 (hereafter, "Hsu 2005"); Rerksuppaphol, L., & Rerksuppaphol, S. (2011). Efficacy of electro-acupuncture at the main acupoints for weight reduction in Thai obese women (hereafter, "Rerksuppaphol 2011").

Applicant has identified a frequency range as low as about 1 Hz and as high as 15 Hz for the ideal stimulation paradigm in this application. This frequency selection is based upon the paradigm used by Cabioglu's group in its six studies, by a transcutaneous electric nerve stimulation study previously mentioned, and by the successful use of manual acupuncture for bringing about weight loss. See e.g., Cabioglu 2008; Cabioglu 2006; Cabioglu, Ergene 2006; Cabioglu 2005; Cabioglu et al 2007; Cabioglu 2007; Tian, D., Li, X., Shi, Y., Liu, Y., & Han, J. (2003). Study on the effect of transcutaneous electric nerve stimulation on obesity. *Beijing da xue xue bao. Yi xue ban=Journal of Peking University. Health sciences,* 35(3), 277. Chinese with English Translation (hereafter, "Tian 2003"); Güçel, F., Bahar, B., Demirtas, C., Mit, S., & Çevik, C. (2012). Influence of acupuncture on leptin, ghrelin, insulin and cholecystokinin in obese women: a randomised, sham-controlled preliminary trial. *Acupuncture in Medicine,* 30(3), 203-207 (hereafter, "Gucel 2012").

Advantageously, Applicant has determined that low current or low intensity stimulation is successful at bringing about weight loss when applied to the acupuncture points previously identified. That this is so may be due, in part, to the fact that there appears to be little electrical resistance at those points. Applicant has identified a suitable intensity between about one and ten milliamps based upon its analysis of the current used in successful acupuncture studies. It does not appear high intensity is required except perhaps with the use of transcutaneous electric nerve stimulation for which the skin must also be penetrated by electrical current. In addition, manual acupuncture, which is not thought to carry as much intensity as high current intensity electroacupuncture, has had a fair amount of success. See, e.g. Gucel 2012, Cheng 2007, Zhi-Cheng, L., Feng-min, S., & Yi-zheng, W. (1995). Good Regulation of Acupuncture in Simple Obesity Patients with Stomach-Intestine Excessive Heat Type [J]. *CHINESE JOURNAL OF INTEGRATED TRADITIONAL AND WESTERN MEDICINE*, 3 (hereafter, "Zhi-cheng 1995"); Li-qiu, L., Wei-zhi, G., & Xin, D. (2005). Treatment of simple obesity of stomach-intestine excessive heat type by acupuncture and Tuina. *Journal of Acupuncture and Tuina Science*, 3(2), 61-62 (hereafter, Li-qiu 2005"); Qunli, W., & Zhicheng, L. (2005). Acupuncture treatment of simple obesity. *J Tradit Chin Med*, 25(2), 90-4 (hereafter, "Qunli 2005"); Zhao, N. X., Guo, R. L., & Ren, Q. Y. (2004). Effect of Acupuncture Treatment on Cellular Hemorheology, Cholesterol and Triglyceride of Simple Obesity Patients. *WORLD JOURNAL OF ACUPUNCTURE MOXIBUSTION—BEIJING—*, 14(3) 24-27 (hereafter, "Zhao 2004").

Because low current stimulation is more ideal for maintaining a small battery size, and further because the combination of manual acupuncture and EA stimulation using low current have proven successful, applicant has chosen to limit its stimulation paradigm to the use of a low stimulation current, e.g., 1 to 10 mA, in combination with a low frequency of stimulation, e.g., 1 to 15 Hz.

Applicant has selected to use a pulse-width range of about 0.1 to 0.5 milliseconds. While the Cabioglu studies utilized a narrower pulse width, Applicant is of the opinion that a narrow pulse width of, e.g., 0.05 milliseconds may prove more difficult in the recruitment of fibers. The chosen pulse width range is in line with one study done by Tian et al. See, Tian 2003.

The 2000 year history of acupuncture supports a fairly short stimulation duration and rate of occurrence. It supports a stimulation session duration as short as 20 minutes (though more ordinarily done in 30 minute durations) and a rate of occurrence of stimulation sessions as short as one occurrence each day and as long as once every other week (though more commonly once a week). Applicant has designed its stimulation paradigm to include an ideal duration and rate of occurrence with both the life of the EA device and a beneficial result for the patient in mind. This stimulation paradigm includes: (1) a duration of stimulation sessions between about 20 minutes and about 60 minutes, and (2) a rate of occurrence of the stimulation sessions of between about once every other week to once daily.

Mechanical Design

Figure 1A:
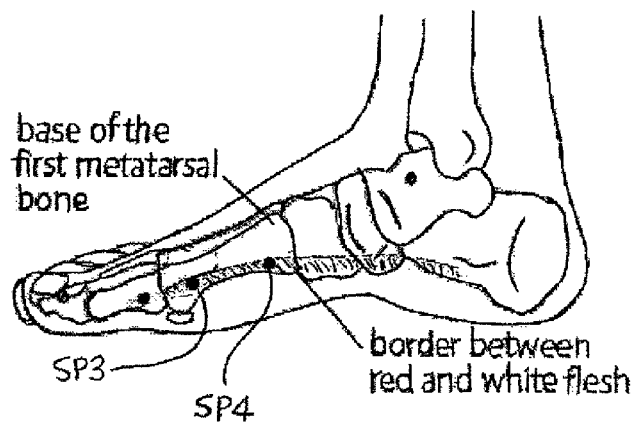
FIG. 1A illustrates the location of acupoint SP4 (referred to herein as Gongsun), one of the three acupoints identified herein that may serve as a target stimulation site at which an IEAD may be implanted for the treatment of obesity.
Figure 1B:
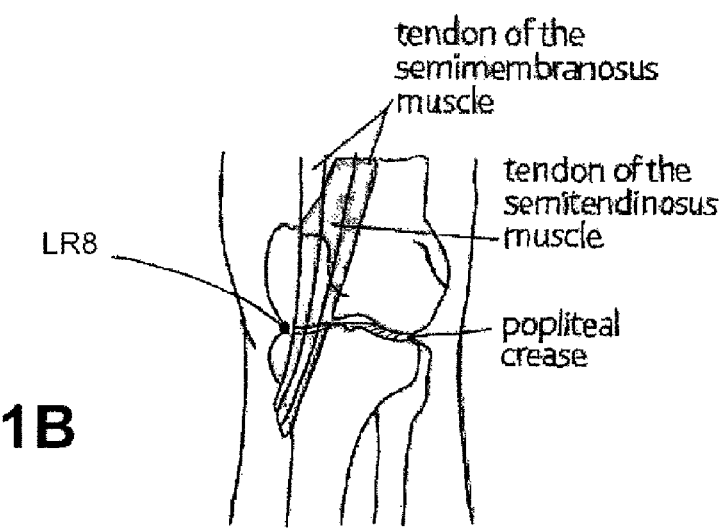
FIG. 1B depicts the location of acupoint LR8 or Ququan, the second of the three acupoints identified herein that may serve as a target stimulation site at which an IEAD may be implanted for the treatment of obesity.
Figure 1C:
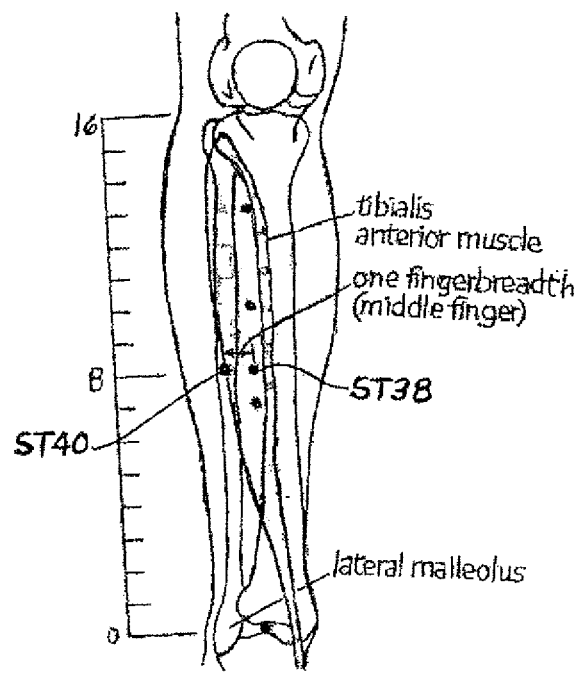
FIG. 1C shows the location of acupoint ST40 or Fenglong, the third of three acupoints identified herein that may serve as a target stimulation site at which an IEAD may be implanted for the treatment of obesity. Note that the notations "first," "second," and "third" do not indicate any priority of one acupoint over another. Also note that these first, second and third acupoints are not the only target stimulation sites that may be used for the treatment of overweight and obese conditions as taught herein. The underlying nerves, saphenous and peroneal, may also serve as a target stimulation site.

Turing first to FIG. 1, there is shown a perspective view of one preferred embodiment of an implantable electroacupuncture device (IEAD) 100 that may be used to treat obese conditions in accordance with the teachings disclosed herein. The IEAD 100 may also sometimes be referred to as an implantable electroacupuncture stimulator (IEAS). As seen in FIG. 1, the IEAD 100 has the appearance of a disc or coin, having a front side 106 (also referred to as the "cathode" side 106), a back side 102 (or "skin" side 106) (not visible in FIG. 1), and an edge side 104.

As used herein, the "front" side (or "cathode" side) of the IEAD 100 is the side that is positioned so as to face the target stimulation point (e.g., the desired acupoint) where EA stimulation is to be applied when the IEAD is implanted. The "back" side (or "skin" side) is the side opposite the front side and is the farthest away from the target stimulation point when the IEAD is implanted. The "edge" of the IEAD is the side that connects or joins the front side to the back side. In FIG. 1, the IEAD 100 is oriented to show the front side 102 and a portion of the edge side 104.

Many of the features associated with the mechanical design of the IEAD 100 shown in FIG. 1 are the subject of a prior U.S. Provisional Patent Application, entitled "Radial Feed-Through Packaging for An Implantable Electroacupuncture Device", Application No. 61/676,275, filed 26 Jul. 2012, which application is incorporated here by reference.

It should be noted here that throughout this application, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 102 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
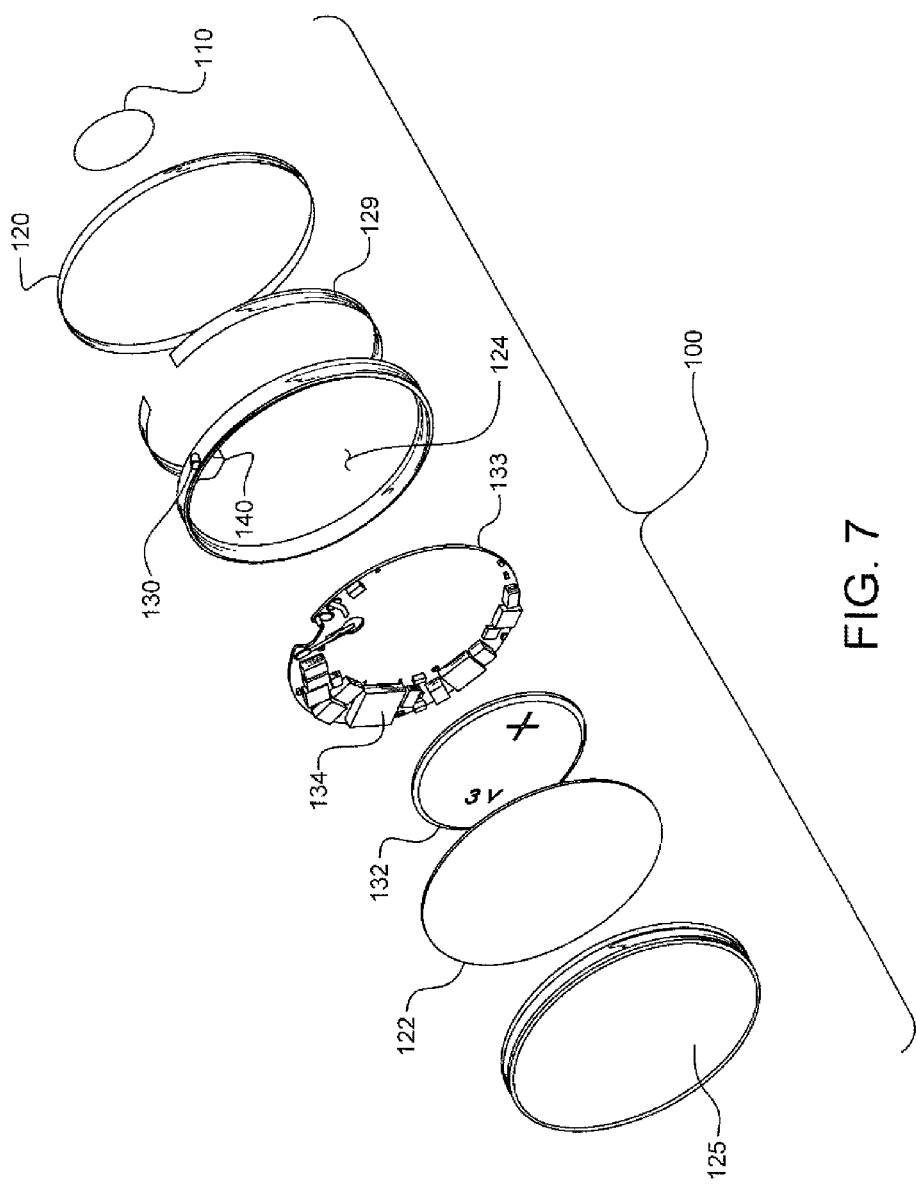
FIG. 7 is an exploded view of the IEAD assembly, illustrating its constituent parts.

The embodiment of the IEAD 100 shown in FIG. 1 utilizes two electrodes, a cathode electrode 110 that is centrally positioned on the front side 106 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the front surface 102 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100, which (for the embodiment shown in FIGS. 1-7) is the front side of the device, faces the target tissue location that is to be stimulated. In addition, the IEAD must be implanted over the desired acupoint, or other tissue location, that is intended to receive the electroacupuncture (EA) stimulation. The orientation of the IEAD 100 is otherwise not important.

Figure 1D:
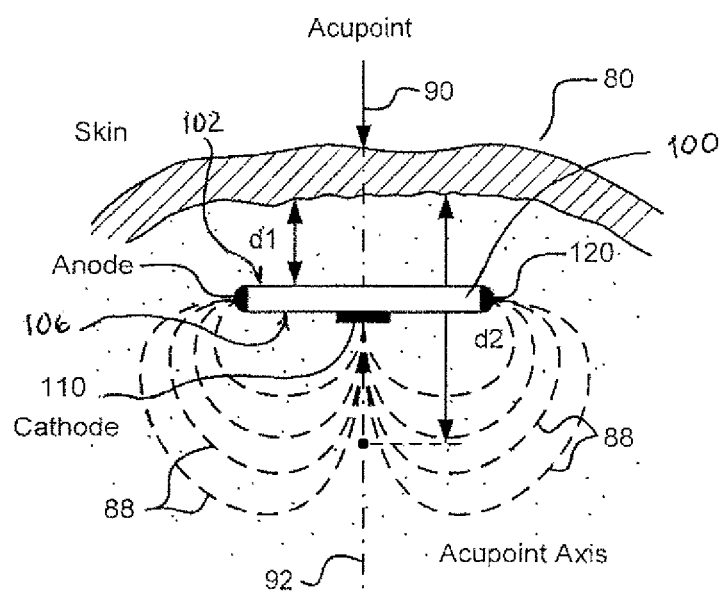
FIG. 1D shows a sectional view of an IEAD implanted at a selected target stimulation site, and illustrates the electric field gradient lines created when an electroacupuncture (EA) pulse is applied to the tissue through the central electrode and ring electrode attached to the bottom surface and perimeter edge, respectively, of the IEAD housing.

Implantation of the IEAD is illustrated in FIG. 1D. Shown in FIG. 1D is a limb 80 of the patient wherein an acupoint 90 has been identified that is to receive acupuncture treatment (in this case electroacupuncture treatment). An incision 82 is made into the limb 80 a short distance, e.g., 10-15 mm, away from the acupoint 90. A slot 84 (parallel to the limb) is formed at the incision by lifting the skin closest to the acupoint up at the incision. As necessary, the surgeon may form a pocket under the skin at the acupoint location. The IEAD 100, with its top side (or skin side) 102 being closest to the skin (and thus also referred to as the "Skin Side"), is then slid through the slot 84 into the pocket so that the center of the IEAD is located under the acupoint 90 on the skin surface. This implantation process is as easy as inserting a coin into a slot. With the IEAD 100 in place, the incision is sewn or otherwise closed, leaving the IEAD 100 under the skin 80 at the location of the acupoint 90 where electroacupuncture (EA) stimulation is desired.

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth d2 that varies depending on the particular acupoint location. When stimulation is applied at the target tissue point, such stimulation is effective at treating a selected condition of the patient, e.g., obesity, because there is something in the tissue at that location, or near that location, such as a nerve, a tendon, a muscle, or other type of tissue, that responds to the applied stimulation in a manner that contributes favorably to the treatment of the condition experienced by the patient.

FIG. 1D shows a sectional view of the IEAD 100 implanted so as to be centrally located under the skin at the selected acupoint 90, and over the acupoint axis line 92. Usually, for most patients, the IEAD 100 is implanted at a depth d1 of approximately 2-4 mm under the skin. The top side 102 of the IEAD is nearest to the skin 80 of the patient (and thus is also referred to as the "skin" side 102). The bottom side 106 of the IEAD, which is the side on which the central cathode electrode 110 resides (and hence is also referred to as the "cathode" side), is farthest from the skin. Because the cathode electrode 110 is centered on the bottom of the IEAD, and because the IEAD 100 is implanted so as to be centered under the location on the skin where the acupoint 90 is located, the cathode 110 is also centered over the acupoint axis line 92.

FIG. 1D further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1D, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the acupoint location indicated on the skin.

FIG. 2 shows a plan view of the "front" (or "cathode") side 106 of the IEAD 100. As seen in FIG. 2, the cathode electrode 110 appears as a circular electrode, centered on the front side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "back" (or "skin") side of the IEAD 100. As will be evident from subsequent figure descriptions, e.g., FIGS. 5A and 5B, the back side of the IEAD 100 comprises a cover plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the cover plate 122 is welded, or otherwise bonded, to the bottom case 124 in order to form the hermetically-sealed IEAD housing 100.

Figure 4:
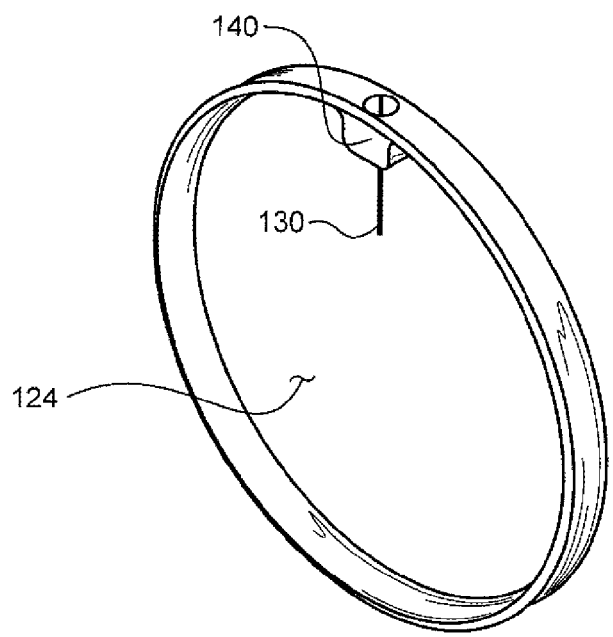
FIG. 4 is a perspective view of the IEAD housing, including a feed-through pin, before the electronic components are placed therein, and before being sealed with a cover plate.

FIG. 4 shows a perspective view of the IEAD case 124, including the feed-through pin 130, before the electronic components are placed therein, and before being sealed with the "skin side" cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
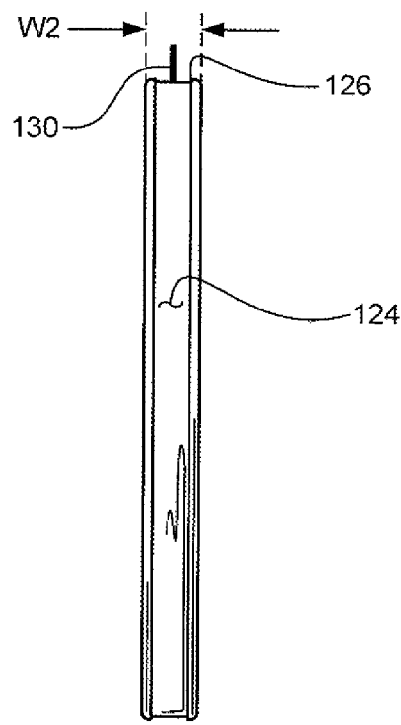
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 7) is placed between the backside of the ring anode electrode 120 and the perimeter edge of the case 124 where the ring anode electrode 120 is placed around the edge of the case 124.

Figures 5, 5A, 5B:
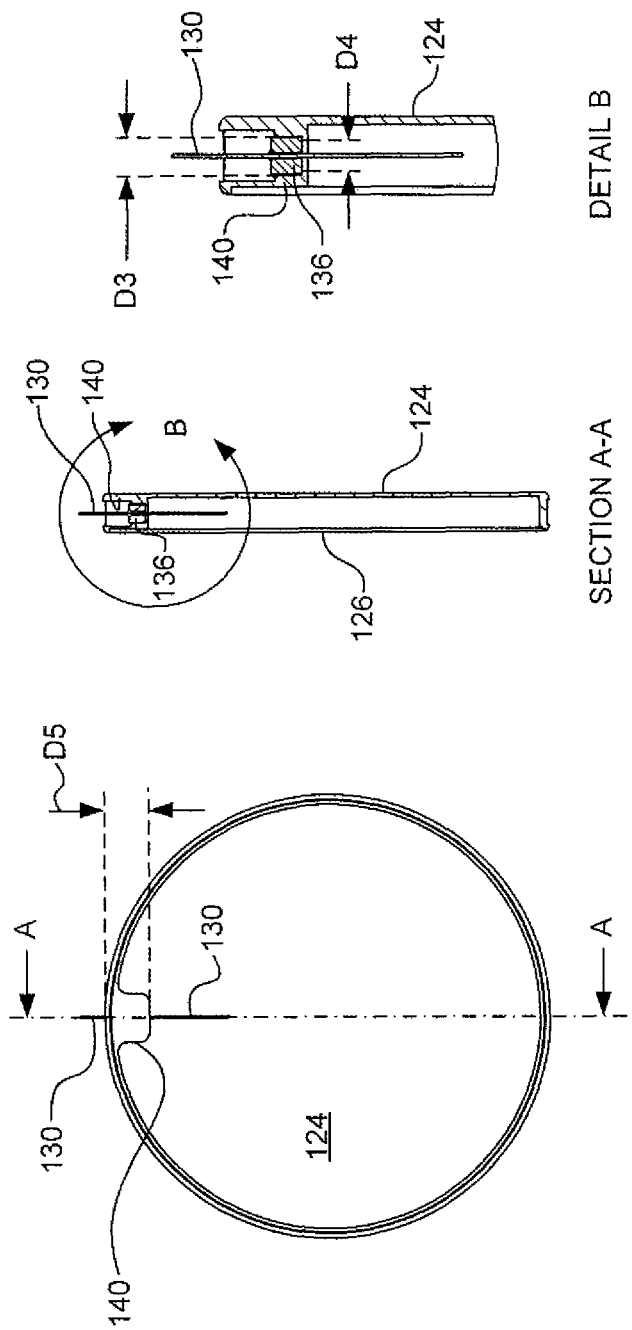
FIG. 5 is a plan view of the empty IEAD housing shown in FIG. 4.
FIG. 5A depicts a sectional view of the IEAD housing of FIG. 5 taken along the section line A-A of FIG. 5.
FIG. 5B shows an enlarged view or detail of the portion of FIG. 5A that is encircled with the line B.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95%. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1\times10^{-9}$ STD cc/sec at 1 atm pressure. Other tests are performed to verify the case-to-pin resistance (which should be at least $15\times10^{6}$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in many of the co-pending patent applications referenced above in Paragraph [0001].

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a pc board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An overmodling process is used to accomplish this, although overmolding using silicone LSR 70 (curing temperature of 120° C.) with an injection molding process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the invention to be used to provide a robust, compact, thin, case to house the electronic circuitry and power source used by the invention; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupuoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a front surface of the housing, one of a first polarity, and a second of a second polarity, could still, when oriented properly with respect to a selected acupoint tissue location, provide some desired therapeutic results.

Figure 7A:
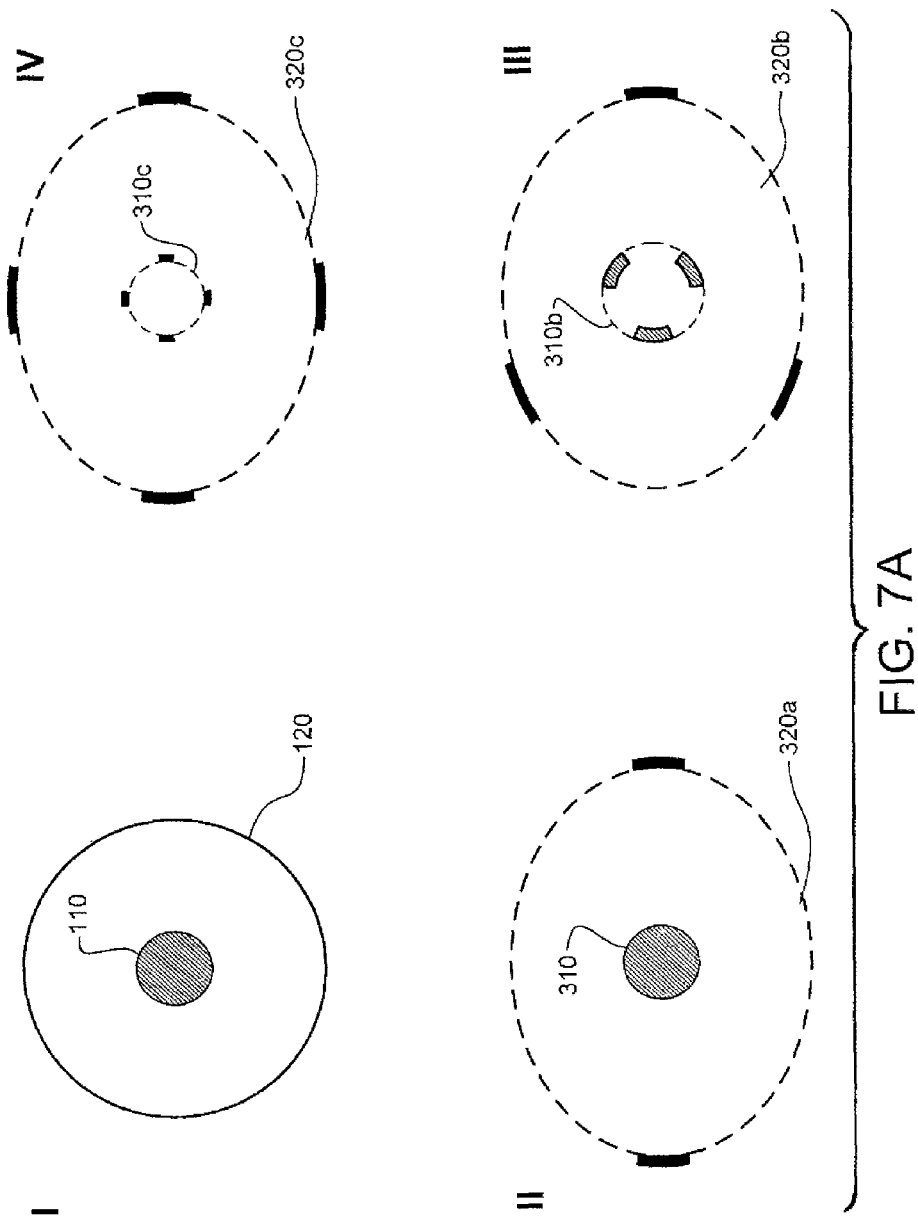
FIG. 7A schematically illustrates a few alternative electrode configurations that may be used with the invention.

FIG. 7A schematically illustrates a few alternative electrode configurations that may be used with the invention. The electrode configuration schematically shown in the upper left corner of FIG. 7A, identified as "I", schematically illustrates one central electrode 110 surrounded by a single round ring electrode 120. This is one of the preferred electrode configurations that has been described previously in connection, e.g., with the description of FIGS. 1-7, and is presented in FIG. 7A for reference and comparative purposes.

In the lower left corner of FIG. 7A, identified as "II", an electrode/array configuration is schematically illustrated that has a central electrode 310 of a first polarity surrounded by an oval-shaped electrode array 320a of two electrodes of a second polarity. (This oval-shaped array 320a could also be round.) When the two electrodes (of the same polarity) in the electrode array 320a are properly aligned with the body tissue being stimulated, e.g., aligned with a nerve 87 (see FIGS. 17A and 17B), then such electrode configuration can stimulate the body tissue (e.g., the nerve 87) at or near the desired acupoint(s) with the same, or almost the same, efficacy as can the electrode configuration I (upper right corner of FIG. 7A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 7A, identified as "III", en electrode configuration is schematically illustrated that has a round central electrode/array 310b of three electrode segments of a first polarity surrounded by an oval-shaped electrode array 320b of three electrode segments of a second polarity. (These round or oval shapes could be altered, as desired or needed. That is, the round central electrode/array 310b could be an oval-shaped electrode array, and the oval-shaped electrode array 320b could be a round electrode array.) As shown in FIG. 7A-III, the three electrode segments of the electrode array 320b are symmetrically positioned within the array 320b, meaning that they are positioned more or less equidistant from each other. However, a symmetrical positioning of the electrode segments within the array is not necessary to stimulate the body tissue at the desired acupoint(s) with some efficacy.

In the upper right corner of FIG. 7A, identified as "IV", an electrode/array configuration is schematically illustrated that has a central electrode array 310c of a first polarity surrounded by an electrode array 320c of four electrode segments of a second polarity. (As explained above in connection with FIG. 7A, III, the round or oval shapes of the electrodes/arrays shown in FIG. 7A, IV, could be altered, as desired or needed.) The four electrode segments of the electrode array 320c are arranged symmetrically in a round or oval-shaped array. The four electrode segments of the electrode array 310b are likewise arranged symmetrically in a round or oval-shaped array. While preferred for many configurations, the use of a symmetrical electrode/array, whether as a central electrode array 310 or as a surrounding electrode/array 320, is not always required.

The electrode configurations I, II, III and IV shown schematically in FIG. 7A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, ... n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

As has already been mentioned, the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are described in Appendix A and Appendix B.

Electrical Design

Next, with reference to FIGS. 8A-14, the electrical design and operation of the circuits employed within the IEAD 100 will be described. More details associated with the design of the electrical circuits described herein may be found in the following previously-filed U.S. Patent Applications, which applications are incorporated herein by reference: (1) application Ser. No. 13/622,497, filed Sep. 19, 2012, entitled Implantable Electroacupuncture Device and Method for Treating Cardiovascular Disease; (2) Appl. No. 61/609,875, filed Mar. 12, 2012, entitled Boost Converter Output Control For Implantable Electroacupuncture Device; (3) Appl. No. 61/672,257, filed Jul. 16, 2012, entitled Boost Converter Circuit Surge Control For Implantable Electroacupuncture Device Using Digital Pulsed Shutdown; (4) Appl. No. 61/672,661, filed Jul. 17, 2012, entitled Smooth Ramp-Up Stimulus Amplitude Control For Implantable Electroacupuncture Device; and (5) Appl. No. 61/674,691, filed Jul. 23, 2012, entitled Pulse Charge Delivery Control In An Implantable Electroacupuncture Device.

Figure 8A:
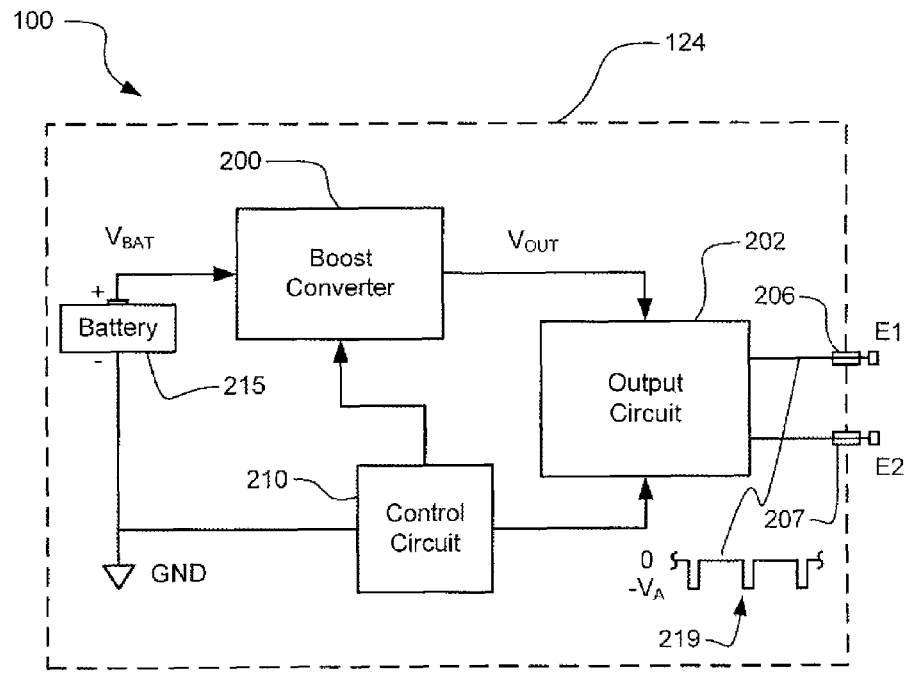
FIG. 8A illustrates a functional block diagram of the electronic circuits used within an IEAD of the type described herein.

FIG. 8A shows a functional block diagram of an implantable electroacupuncture device (IEAD) 100 made in accordance with the teachings disclosed herein. As seen in FIG. 8A, the IEAD 100 uses an implantable battery 215 having a battery voltage $V_{BAT}$. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

Figure 15A:
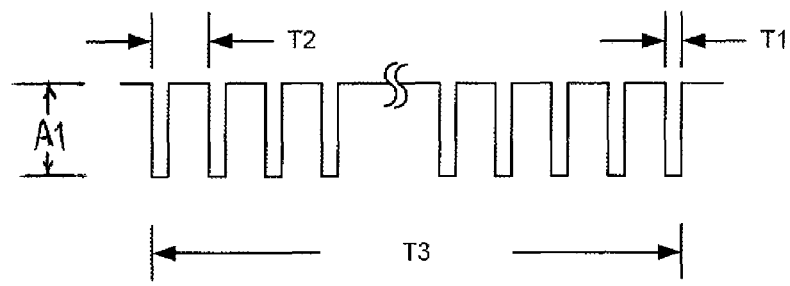
FIG. 15A shows a timing waveform diagram of representative EA stimulation pulses generated by the IEAD device during a stimulation session.

As explained more fully below in connection with the description of FIGS. 15A and 15B, the prescribed stimulation regimen comprises a continuous stream of stimulation pulses having a fixed amplitude, e.g., $V_A$ volts, a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week. Other stimulation regimens may also be used, e.g., using a variable frequency for the stimulus pulse during a stimulation session rather than a fixed frequency.

In one preferred embodiment, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and low duty cycles in accordance with specified stimulation regimens through electrodes that form an integral part of the housing of the stimulator. A tiny battery inside of the coin-sized stimulator provides enough energy for the stimulator to carry out its specified stimulation regimen over a period of several years. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
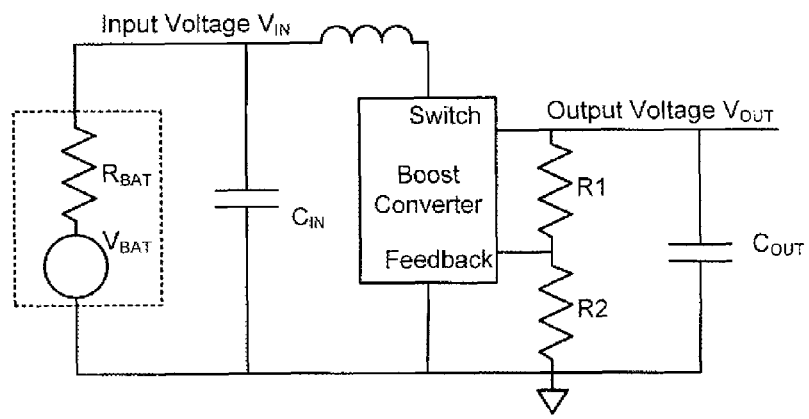
FIG. 8B shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 8A, the battery is modeled as a voltage source with a simple series resistance. With reference to the circuit shown in FIG. 8A, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
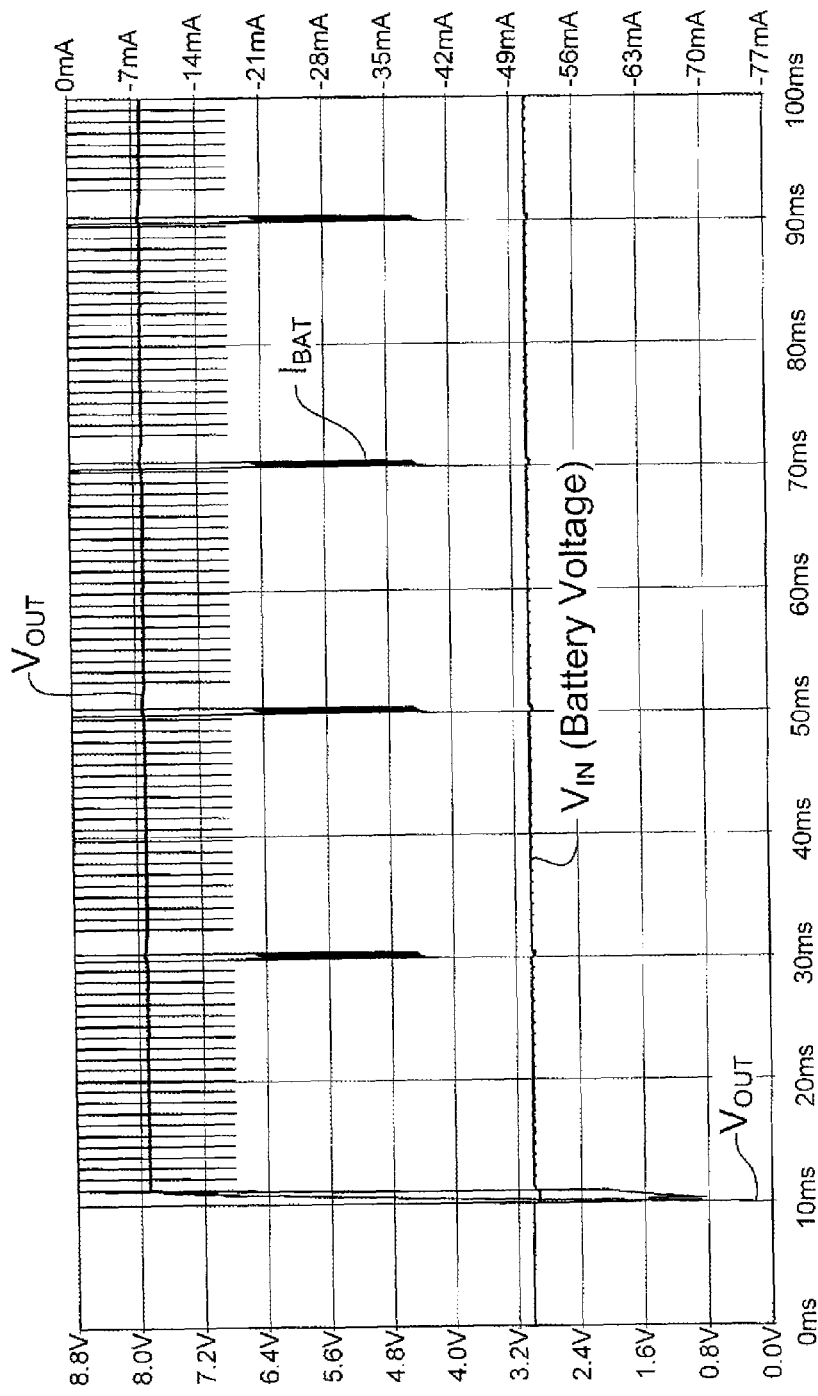
FIG. 9A illustrates a typical voltage and current waveform for the circuit of FIG. 8 when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 9B:
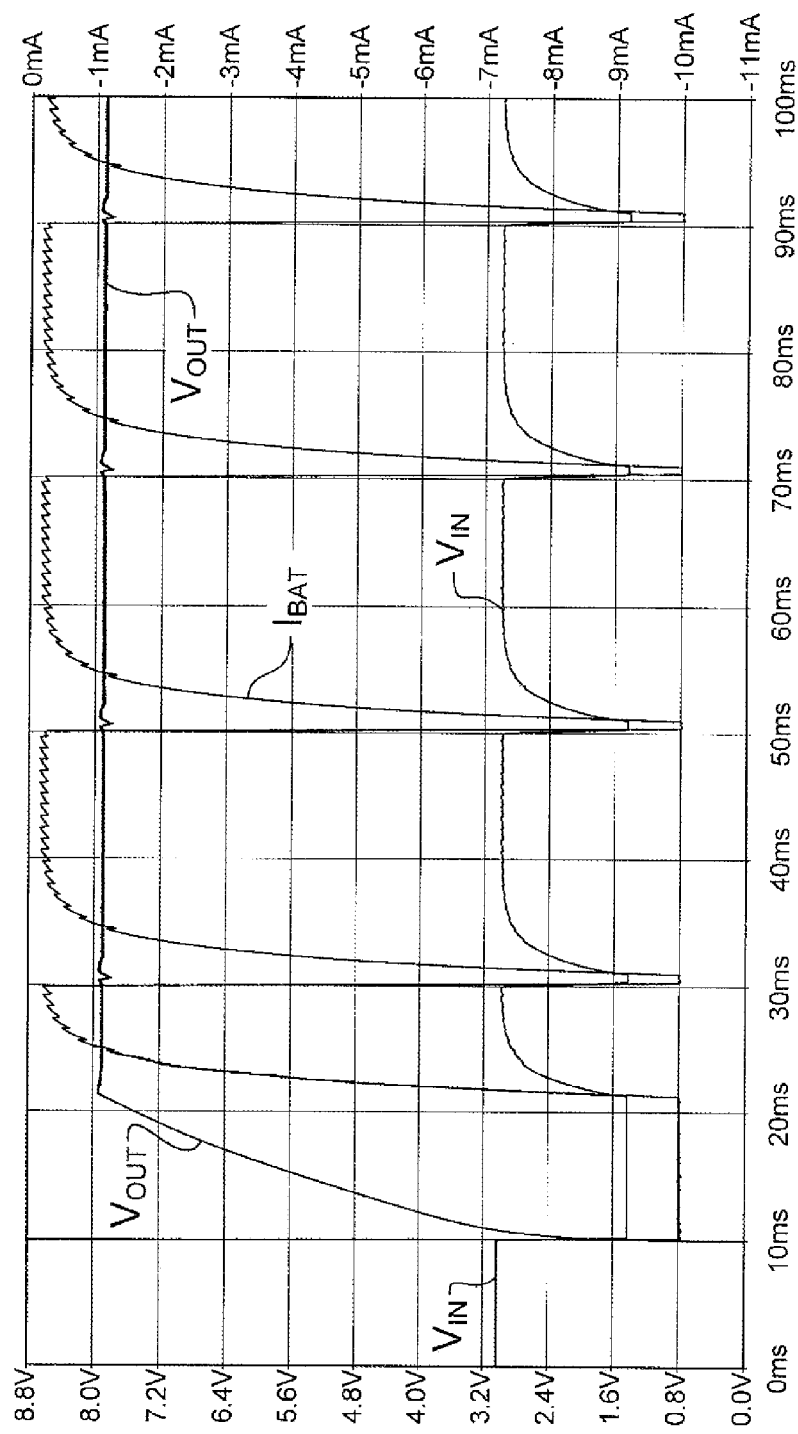
FIG. 9B shows the voltage and current waveform for the circuit of FIG. 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electro-acupuncture stimulus pulses. The resulting drops in output voltage $V_{OUT}$ are just not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when EA stimulation pulses are generated.

Figure 10:
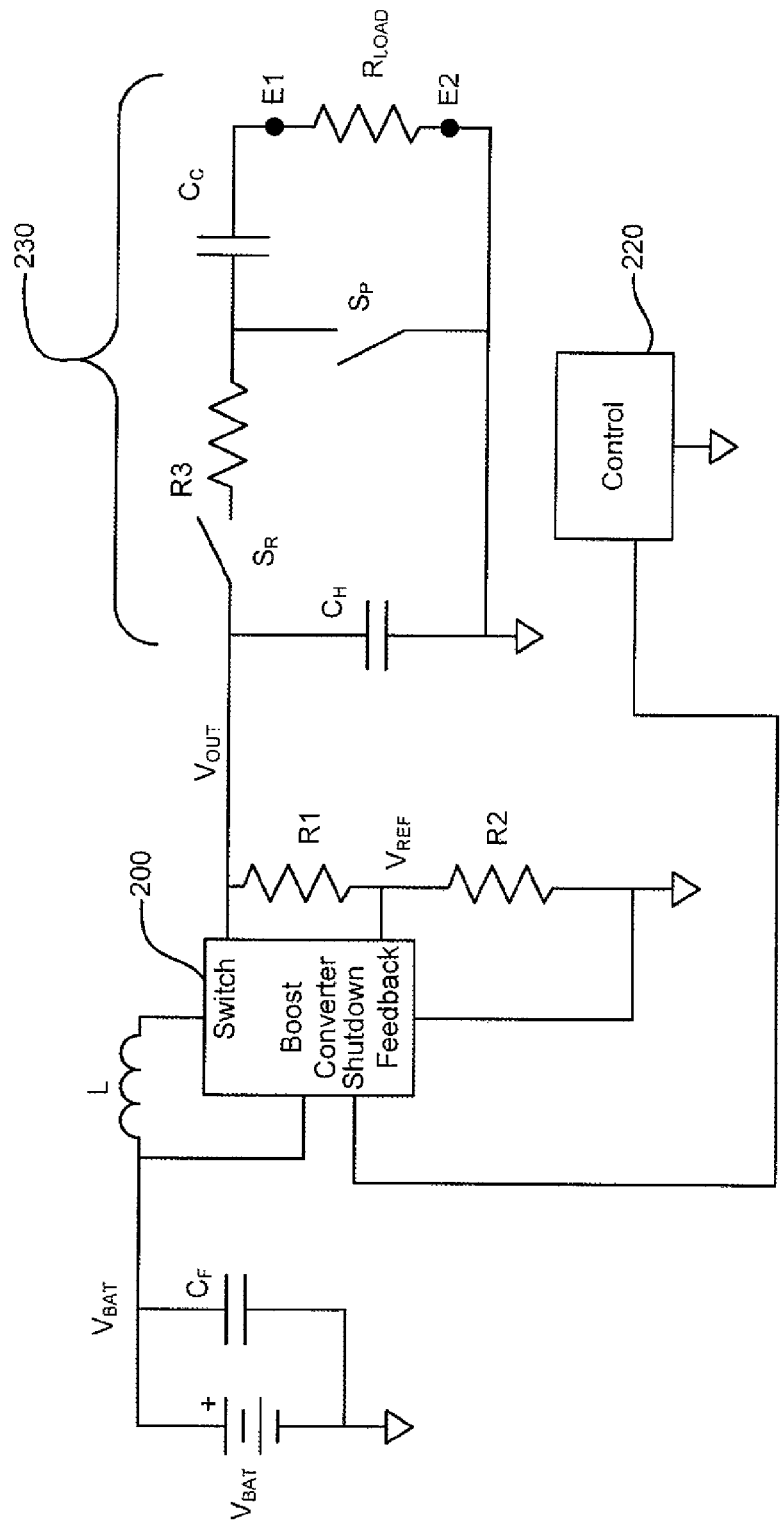
FIG. 10 shows one preferred boost converter circuit and a functional pulse generation circuit configuration for use within the IEAD.

To provide this needed current management, the IEAD 100 disclosed herein employs electronic circuitry as shown in FIG. 10, or equivalents thereof. Similar to what is shown in FIG. 8B, the circuitry of FIG. 10 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

Figure 11:
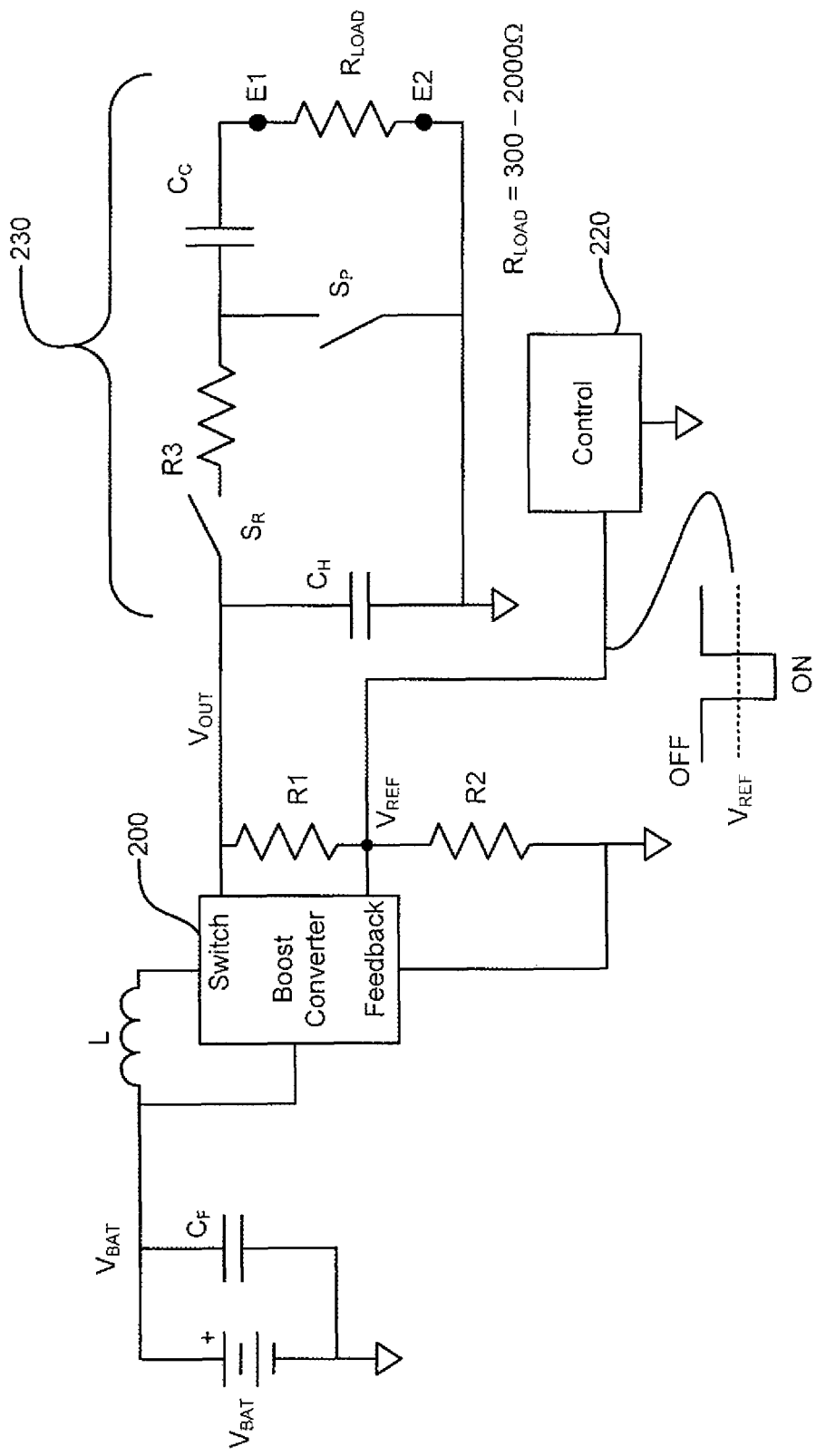
FIG. 11 shows an alternate boost converter circuit configuration and a functional pulse generation circuit for use within the IEAD.

An alternate embodiment of the electronic circuitry that may be used within the IDEA 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning the boost converter circuit ON.

Figure 12:
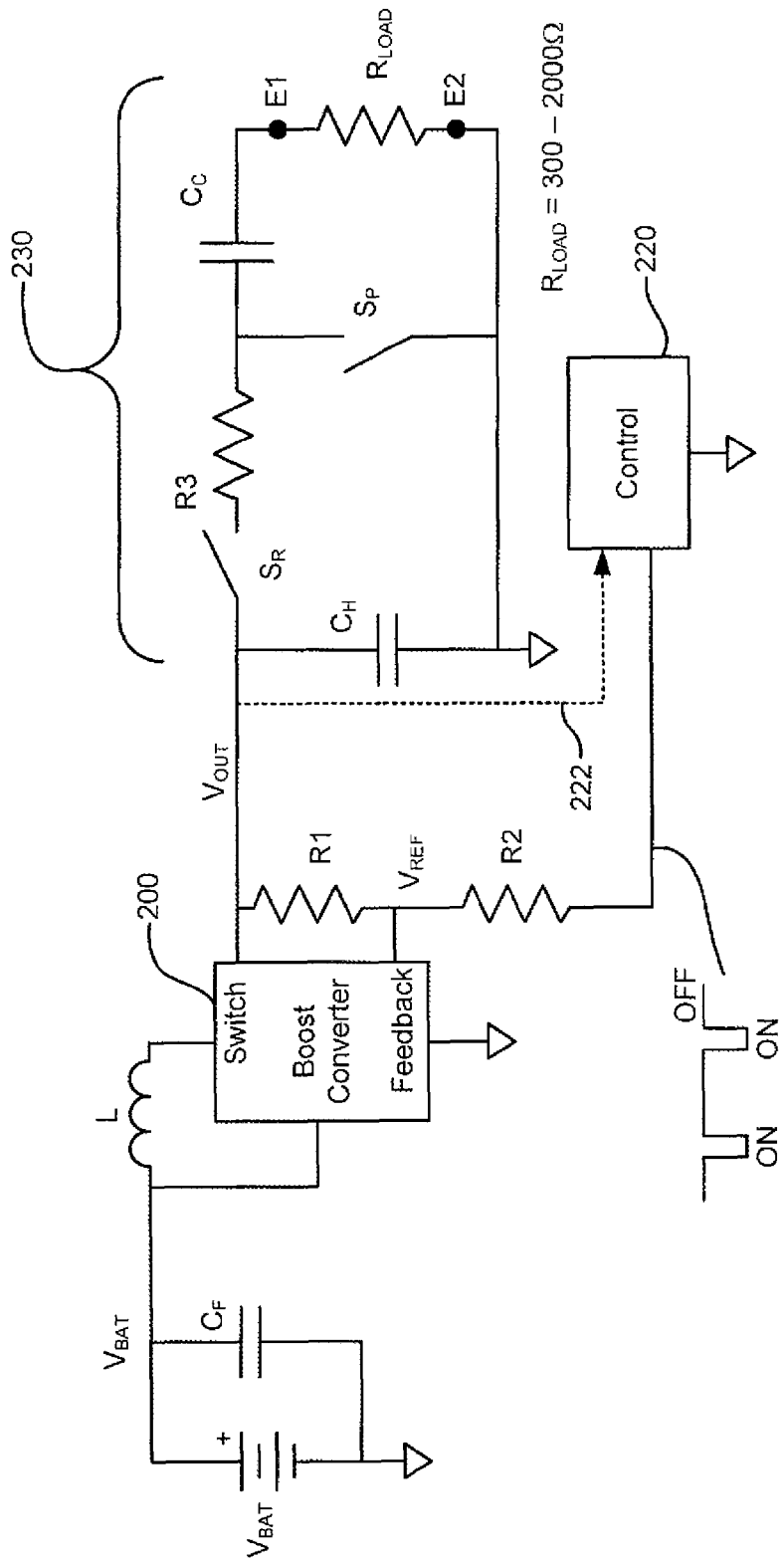
FIG. 12 shows a refinement of the circuit configuration of FIG. 11.

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
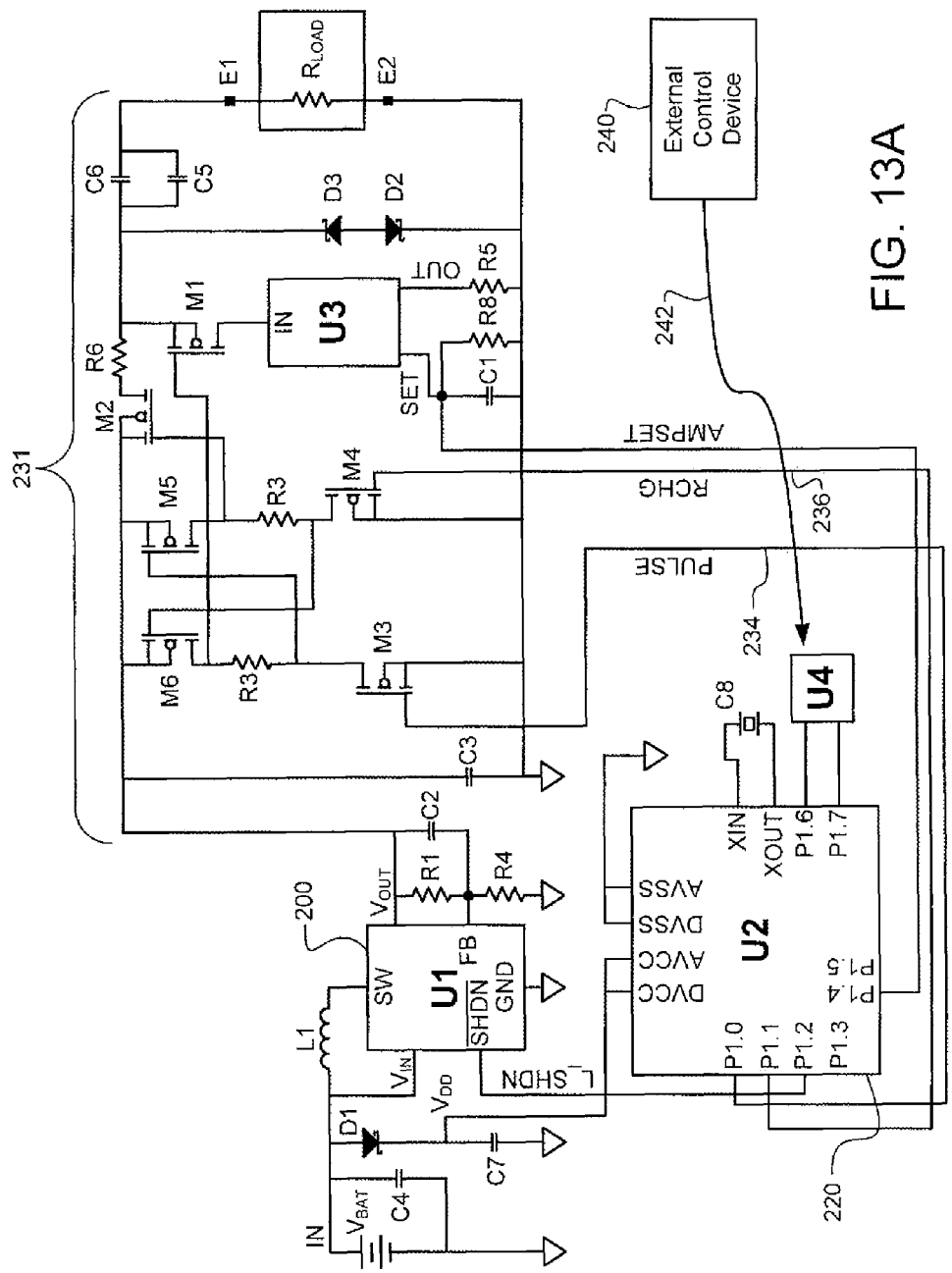
FIG. 13A shows one preferred schematic configuration for an implantable electroacupuncture device (IEAD) that utilizes the boost converter configuration shown in FIG. 10.

One preferred embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. A preferred IC for this purpose is a MSP430G24521 micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straightforward manner.

The micro-controller U2 primarily performs the function of generating the digital signal that shuts down the boost converter to prevent too much instantaneous current from being drawn from the battery $V_{BAT}$. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

It is also important that the circuitry used in the IEAD 100, e.g., the circuitry shown in FIGS. 10, 11, 12, 13A, or equivalents thereof, have some means for controlling the stimulation current that flows through the load, $R_{LOAD}$, which load may be characterized as the patient's tissue impedance at and around the acupoint being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 13A by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
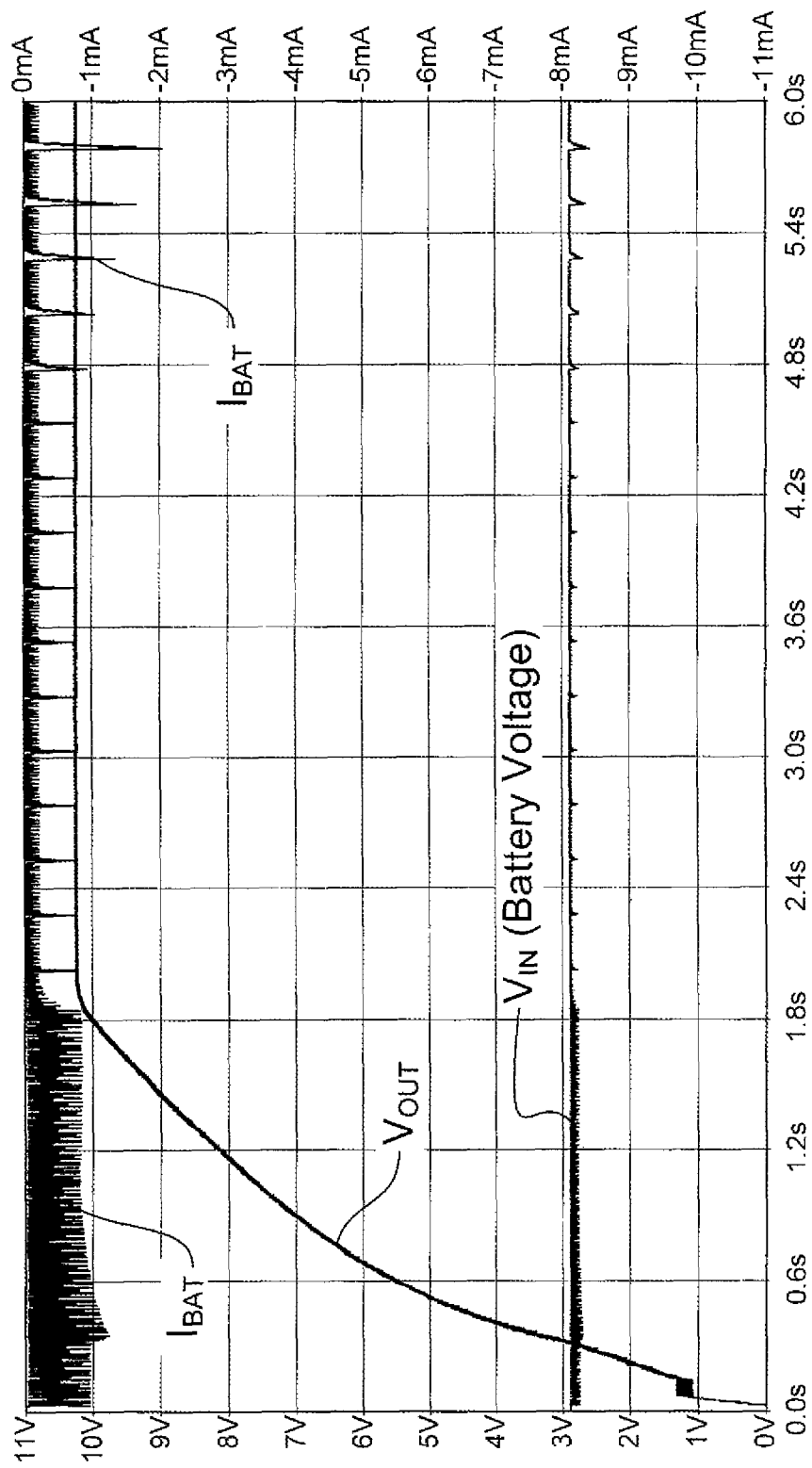
FIG. 13B shows current and voltage waveforms associated with the operation of the circuit shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13A have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
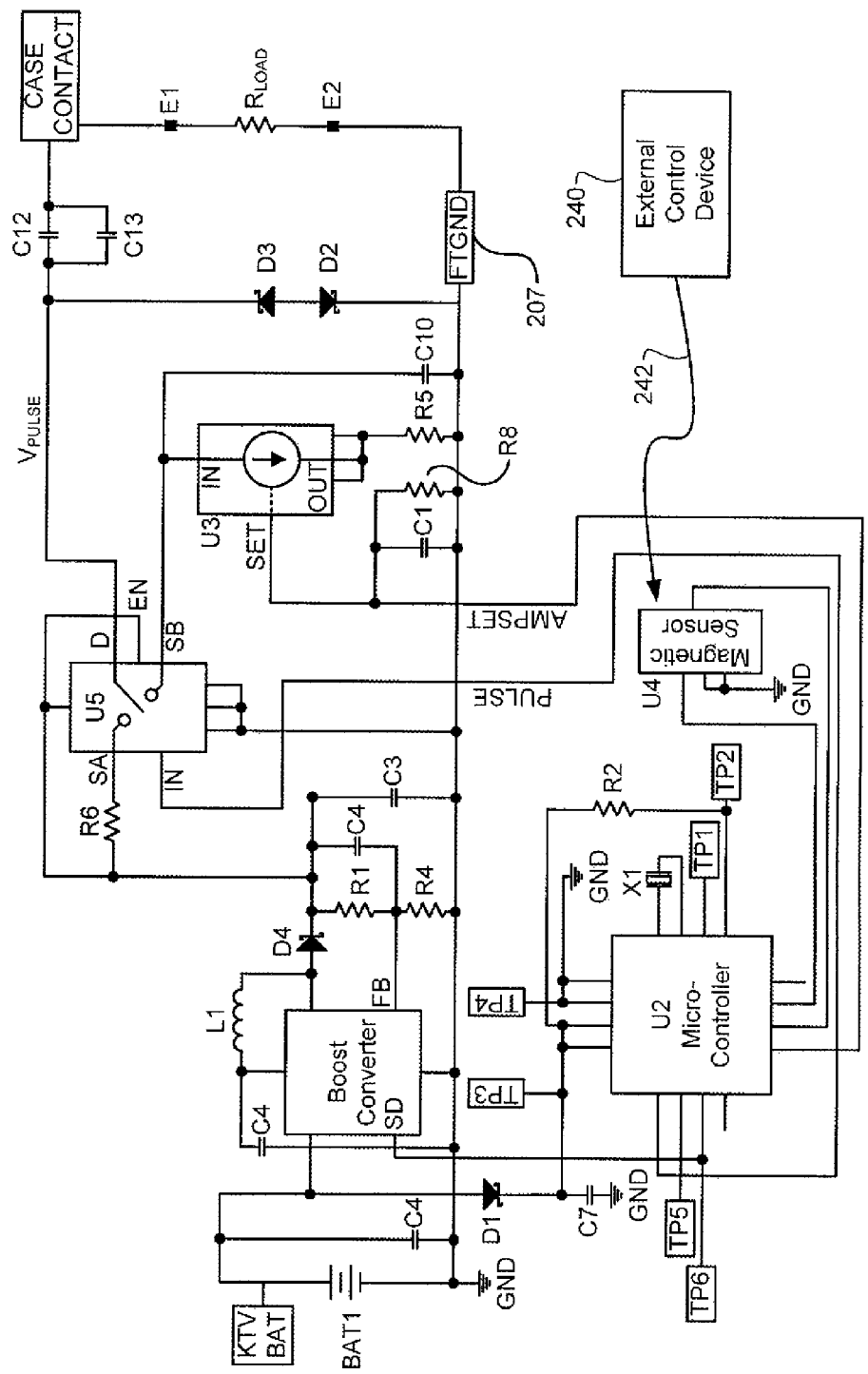
FIG. 14 shows another preferred schematic configuration for an IEAD similar to that shown in FIG. 13A, but which uses an alternate output circuitry configuration for generating the stimulus pulses.

Another preferred embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of an external Schottky diode D4 at the output terminal LX of the boost convertor U1 and the inclusion of a fifth integrated circuit (IC) U5 that essentially performs the same function as the switches M1-M6 shown in FIG. 13A.

The Schottky diode D5 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (electromagnetic sensor) are basically the same as the IC's U1, U2, U3 and U4 described previously in connection with FIG. 13A.

The IC U5 shown in FIG. 14 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

From the above description, it is seen that an implantable IEAD 100 is provided that uses a digital control signal to duty-cycle limit the instantaneous current drawn from the battery by a boost converter. Three different exemplary configurations (FIGS. 10, 11 and 12) are taught for achieving this desired result, and two exemplary circuit designs that may be used to realize this result have been disclosed (FIGS. 13A and 14). One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, Delta-sigma modulation.

II. F. Use and Operation

With the implantable electroacupuncture device (IDEA) 100 in hand, the IDEA 100 may be used most effectively to treat overweight conditions by first pre-setting stimulation parameters that the device will use during a stimulation session. FIG. 15A shows a timing waveform diagram illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is defined by the time period T3. The amplitude of the stimulus pulses is defined by the amplitude A1. This amplitude may be expressed in either voltage or current.

Figure 15B:
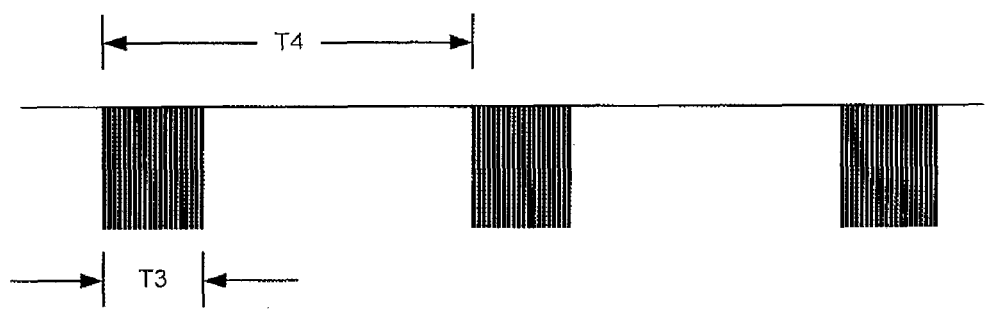
FIG. 15B shows a timing waveform diagram of multiple stimulation sessions, and illustrates the waveforms on a more condensed time scale.

Turning next to FIG. 15B, a timing waveform diagram is shown that illustrates the manner in which the stimulation sessions are administered in accordance with a preferred stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4(min). Then, as time goes on, the value of T4 is gradually increased until a desired value of T4, T4(final) is reached.

By way of example, if T4(min) is 1 day, and T4(final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table of session durations and intervals whereby the automatic session interval can be shorter for the first week or so. For example the $1^{st}$ 30 minute session could be delivered after 1 day. The $2^{nd}$ 30 minute session could be delivered after 2 days. The $3^{rd}$ 30 minute session could be delivered after 4 days. Finally, the $4^{th}$ 30 minute session could be delivered for all subsequent sessions after 7 days.

If a triggered session is delivered completely, it advances the therapy schedule to the next table entry.

Another enhancement is that the initial set amplitude only takes effect if the subsequent triggered session is completely delivered. If the first session is aborted by a magnet application, the device reverts to a Shelf Mode. In this way, the first session is always a triggered session that occurs in the clinician setting.

Finally, the amplitude and place in the session table are saved in non-volatile memory when they change. This avoids a resetting of the therapy schedule and need to reprogram the amplitude in the event of a device reset.

One preferred set of parameters to use to define a stimulation regimen are

T1=0.5 milliseconds
T2=500 milliseconds
T3=30 minutes
T4=7 days (10,080 minutes)
A1=6 volts (across 1 kOhm), or 6 milliamperes (mA)

It is to be emphasized that the values shown above for the stimulation regimen are representative of only one preferred stimulation regimen that could be used. Other stimulation regimens that could be used, and the ranges of values that could be used for each of these parameters, are as defined in the claims.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired acupuncture site, but it also limits the frequency and duration of stimulation sessions.

Limiting the frequency and duration of the stimulation sessions is a key aspect of applicants' invention because it recognizes that some treatments, such as treating overweight conditions, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce the sustained therapeutic effect. Thus, applicants have based their treatment regimens on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit 220, the IEAD 100 needs to be implanted. Implantation is usually a simple procedure, and is described above in connection, e.g., with the description of FIGS. 1A, 1B, 1C and 1D.

For treating obesity as targeted by the invention described herein, the specified acupoint(s) (or target tissue locations) at which the EA stimulation pulses should be applied in accordance with a selected stimulation regimen are the acupoints SP4, LR8 and/or ST40, or their underlying nerves. As indicated previously, acupoint SP4 is located on the medial side of the foot in the depression distal to the base of the first metatarsal bone. See FIG. 1B and *WHO Standard Acupuncture Point Locations* 2008, page 71. Acupoint LR8 is located on the on the medial aspect of the knee in the depression medial to the tendons of the semiteninosus and semimenbranosus muscles at the medial end of the popliteal crease. See FIG. 1C and *WHO Standard Acupuncture Point Locations* 2008, page 199. Acupoint ST40 is located on the anterolateral aspect of the leg at the lateral border of the tibialis anterior muscle, about 8 B-cun superior to the prominence of the lateral malleolus. See FIG. 1C and *WHO Standard Acupuncture Point Locations* 2008, pages 11-13, 66.

Figure 16:
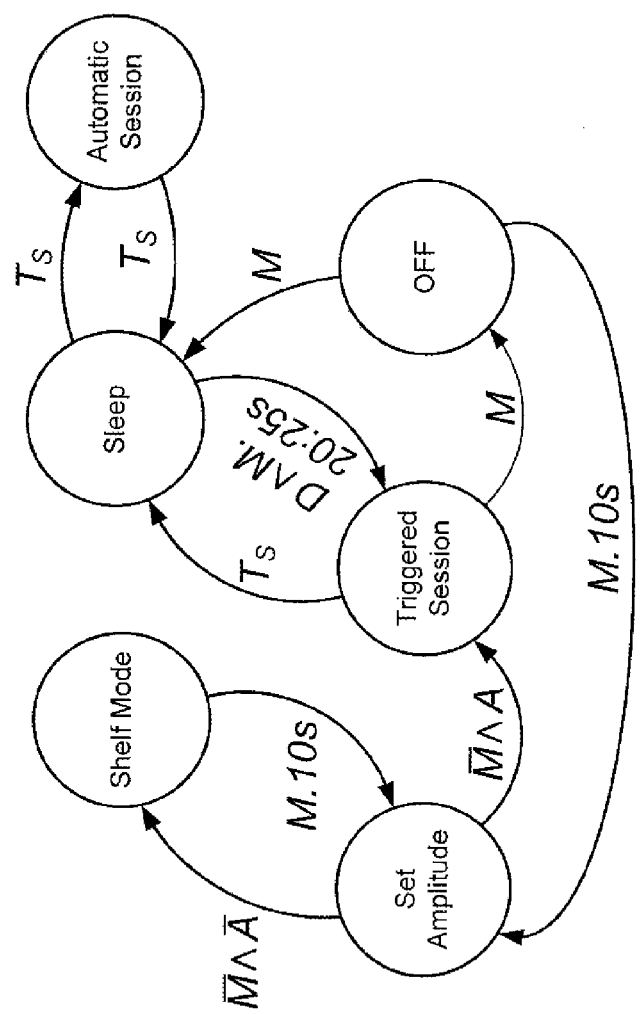
FIG. 16 shows a state diagram that shows the various states the IEAD may assume as controlled by an external magnet.

After implantation, the IEAD must be turned ON, and otherwise controlled, so that the desired stimulation regimen or stimulation paradigm may be carried out. In one preferred embodiment, control of the IEAD after implantation, as well as anytime after the housing of the IEAD has been hermetically sealed, is performed as shown in the state diagram of FIG. 16. Each circle shown in FIG. 16 represents an operating "state" of the micro-controller U2 (FIG. 13A or 14). As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M·10 s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero (M AA), the device continues into the "Triggered Session" so the patient receives the initial therapy. If the magnet is removed during "Set Amplitude" while the amplitude is zero ($\overline{M}\hat{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M·10 s) while in the "OFF" state, the "Set Amplitude" state is entered with the stimulation level starting from zero amplitude as described.

If the magnet is removed (M) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M·20:25 s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in Appendix C, attached hereto, and incorporated by reference herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense and are not intended to be exhaustive or to limit the invention to any precise form disclosed. Many modifications and variations are possible in light of the above teaching. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. A method of treating obesity and overweight conditions in a patient using a small, leadless, coin-sized and coin-shaped, self-contained, implantable electroacupuncture device (IEAD) powered by a small disc primary battery having a specified nominal output voltage of 3 volts, and having an internal impedance of at least 5 ohms, the IEAD being configured, using electronic circuitry within the IEAD, to generate electroacupuncture (EA) stimulation pulses in accordance with a specified stimulation regimen and apply the EA stimulation pulses through at least two electrodes/arrays located on the housing of the IEAD to the patient's body tissue at a selected target tissue stimulation site, said at least two electrodes/arrays comprising a symmetrical electrode configuration that includes at least one central electrode/array of a first polarity, having a maximum width of no more than 7 mm, centrally located on a first surface of the small IEAD housing, and at least one annular electrode/array of a second polarity spaced apart from the central electrode/array by at least 5 mm measured from the edge of the annular electrode/array closest to the central electrode/array to the center of the central electrode/array, said method comprising:

(a) implanting the IEAD below the skin surface of the patient at the selected target stimulation site, the target stimulation site being selected from the group of target stimulation sites comprising acupoints SP4, LR8 and ST40, and underlying nerves saphenous and peroneal, with the first surface of the IEAD facing inwardly into the patient's body tissue at the selected target stimulation site;

(b) enabling the IEAD to continuously provide stimulation pulses in accordance with a stimulation regimen that is configured to slowly and methodically remodel the central nervous system of the patient to provide provides a stimulation session at a rate of once every T4 minutes, with each stimulation session having a duration of T3 minutes, where T3 is at least 10 minutes, and where the ratio of T3/T4 is no greater than 0.05.

2. The method of claim 1 further including setting the time T4 to be at least 1440 minutes [1 day], but no more than about 20,160 minutes [14 days].

3. The method of claim 2 further including setting T3, the duration of the stimulation session, to a value between 20 minutes and 60 minutes.

4. The method of claim 2 further including setting the stimulation pulses during a stimulation session to have a duration of T1 seconds, that occur at a rate of once every T2 seconds, where the ratio of T1/T2 is no greater than 0.01.

5. The method of claim 4 further including setting the time T1 to be 0.1 to 1.0 millisecond and the time T2 to be 250 to 1000 milliseconds.

6. The method of claim 1 further including controlling the electronic circuits within the IEAD to limit instantaneous current drawn from the small disc primary battery so that the output voltage of the primary battery does not drop more than about 11% below the output voltage of the primary battery when current is being drawn from the primary battery, where the output voltage of the primary battery is equal to the specified nominal output voltage of the primary battery less the voltage drop caused by the instantaneous current flowing through the internal impedance of the primary battery.

7. The method of claim 6 wherein the electronic circuitry within the IEAD includes a boost converter circuit, and wherein the method of controlling the electronic circuits within the IEAD to limit the instantaneous current drawn from the battery comprises modulating the operation of the boost converter circuit between an ON state and an OFF state.

* * * * *